(12) United States Patent
Madras et al.

(10) Patent No.: US 6,677,338 B2
(45) Date of Patent: Jan. 13, 2004

(54) SEROTONIN TRANSPORT INHIBITORS

(75) Inventors: Bertha K. Madras, Newton, MA (US);
Peter C. Meltzer, Lexington, MA (US)

(73) Assignees: President and Fellows of Harvard College, Cambridge, MA (US);
Organix, Inc., Woburn, MA (US)

( * ) Notice: Subject to any disclaimer, the term of this patent is extended or adjusted under 35 U.S.C. 154(b) by 0 days.

(21) Appl. No.: 10/085,482

(22) Filed: Feb. 28, 2002

(65) Prior Publication Data

US 2003/0105096 A1 Jun. 5, 2003

Related U.S. Application Data

(60) Continuation of application No. 10/097,062, filed on Mar. 13, 2002, which is a continuation of application No. 09/875,523, filed on Jun. 6, 2001, which is a continuation of application No. 09/671,534, filed on Sep. 27, 2000, which is a division of application No. 09/314,441, filed on May 19, 1999, which is a division of application No. 08/893,921, filed on Jul. 11, 1997, now Pat. No. 5,948,933.
(60) Provisional application No. 60/328,523, filed on Oct. 10, 2001.

(51) Int. Cl.[7] .................... A61K 31/352; A61K 31/382; A61K 31/445; C07D 265/30; C07D 295/00
(52) U.S. Cl. .................... 514/238.8; 514/320; 514/432; 514/456; 544/173; 544/111; 546/192; 546/200; 549/23; 549/283; 549/285; 549/397
(58) Field of Search .............................. 514/238.8, 320, 514/432, 456; 544/111, 173; 546/192, 200; 549/23, 397, 283, 285

(56) References Cited

U.S. PATENT DOCUMENTS

| | | |
|---|---|---|
| 3,813,404 A | 5/1974 | Clark et al. |
| 4,434,151 A | 2/1984 | Byrne et al. |
| 4,499,099 A | 2/1985 | Watts |
| 4,673,562 A | 6/1987 | Davison et al. |
| 4,746,505 A | 5/1988 | Jones et al. |
| 5,122,361 A | 6/1992 | Kung et al. |
| 5,128,118 A | 7/1992 | Carroll et al. |
| 5,310,912 A | 5/1994 | Neumeyer et al. |
| 5,334,728 A | 8/1994 | Kung et al. |
| 5,380,848 A | 1/1995 | Kuhar et al. |
| 5,413,779 A | 5/1995 | Kuhar et al. |
| 5,426,189 A | 6/1995 | Kung et al. |
| 5,439,666 A | 8/1995 | Neumeyer et al. |
| 5,493,026 A | 2/1996 | Elmaleh et al. |
| 5,496,953 A | 3/1996 | Kuhar et al. ................ 546/125 |
| 5,760,055 A | 6/1998 | Davies ........................ 514/304 |
| 5,770,180 A | 6/1998 | Madras et al. .............. 424/1.81 |
| 5,980,860 A | 11/1999 | Kung et al. |
| 6,008,227 A | 12/1999 | Davies et al. ................ 514/304 |
| 6,350,758 B1 | 2/2002 | Kozikowski et al. |
| 6,358,492 B1 | 3/2002 | Kuhar et al. ................ 424/1.85 |

FOREIGN PATENT DOCUMENTS

| | | |
|---|---|---|
| EP | 0 135 160 A2 | 3/1985 |
| WO | WO 93/09814 | 5/1993 |
| WO | WO 95/11901 | 5/1995 |
| WO | WO 97/14445 | 4/1997 |
| WO | WO 97/16210 | 5/1997 |
| WO | WO 97/47328 | 12/1997 |
| WO | WO 98/24788 | 6/1998 |
| WO | WO 99/02526 | 1/1999 |
| WO | 234882 A | 11/2000 |

OTHER PUBLICATIONS

Brandau, et al., *Nucl. Med. Biiol.* (1994) vol. 21, No. 8, pp. 1073–1081.
Bryson, et al., *Inorg. Chem.* (1988), 27, pp. 2154–2161.
Davison, et al., *Inorg. Chem.* (1981) vol. 20, No. 6, pp. 1629–1632.

(List continued on next page.)

*Primary Examiner*—Taofiq A. Solola
(74) *Attorney, Agent, or Firm*—George W. Neuner, Esq.; Gregory B. Butler, Esq.

(57) ABSTRACT

The present invention relates to the therapeutic use of non-amine tropane analogues that bind to the SERT to treat neuropsychiatric disorders.

25 Claims, 4 Drawing Sheets

OTHER PUBLICATIONS

DiZio, et al., *Bioconjugate Chemistry*, (1991) vol. 2, No. 5, pp. 353–366.

DiZio, et al., *Journal of Nuclear Medicine* (1992) vol. 33, No. 4, pp. 558–569.

Fritzberg, et al., *J. Nucl. Med.* (1981) vol. 22, No. 3, pp. 258–263.

Fritzberg, et al., *J. Nucl. Med.* (1982)vol. 23, No. 7, pp. 592–598.

Gustavson, et al., NeoRx Corp, Seattle, WA 98119, pp. 5485–5488.

Hansen, et al., *J. Nuc. Med.* (1994) vol. 35, No. 7, pp. 1198–1205.

Jones, et al., *J. Nucl. Med*, (1982)vol. 23, No. 9, pp. 801–809.

Steigman, et al., *National Academy Press* NAS–NS–3204 Prepared for the Committee on Nuclear and Radiochemistry, National Research Council (1992) pp. 117–127.

Davies, et al, *J. med. Chem*, (1994) vol. 37, No. 9, pp. 1262–1268.

Bennett, et al., *J. of Pharmacology* (1995) vol. 272, No. 3, pp. 1176–1186.

Rao, et al., Eighth International Symposium on Radiopharmaceutical Chemistry, Princeton Univ. (1990) pp. 39–40.

Johannsen, et al., *Eleventh Intern. Symposium Radiopharmaceutical Chem. Abstracts* pp. 319–320.

Agoston, et al., *Amer. Chem. Society*, (1997) vol. 40, No. 26, pp. 4329–4339.

Carroll, et al., *J. Med. Chem.* (1993) vol. 36, No. 20, pp. 2886–2890.

Casy, et al., *J. Pharm. Pharmacol.* (1992)vol. 44, pp. 787–790.

Daum, et al., *J. Med. Chem* (1975), vol. 18, No. 5, pp. 496–501.

Holmquist, et al., *J. Med. Chem* (1996), vol. 39, No. 21, pp. 4139–4141.

Meegalla, et al., *J. Am. Chem. Soc.* (1995) vol. 117, No. 44, pp. 11037–11038.

Meegalla, et al., *J. Am. chem. Soc.* (1996) vol. 7, No. 4, pp. 421–429.

Clarke, et al., *J. Med. Chem.* (1973) vol. 16, No. 11, pp. 1260–1267.

Ohmomo, et al., *J. Med. Chem.* (1992) vol. 35, No. 1, pp. 157–162.

Carroll, et al., *J. Med. Chem.* (1995) vol. 38, No. 2, pp. 379–388.

Kline, et al., *J. Med. Chem.* (1997) vol. 40, No. 6, pp. 851–857.

Meltzer, et al., *J. Med. Chem.* (1996) vol. 39, No. 2, pp. 371–379.

Meltzer, et al., *J. Med. Chem.* (1997) vol. 40, No. 17, pp. 2661–2673.

Meltzer, et al., *J. Med. Chem* (1994) vol. 37, No. 13, pp. 2001–2010.

Newman, et al., *J. Med. Chem.* (1999) vol. 42, No. 18, pp. 3502–3509.

Newman, et al., *J. Med. Chem.* (1995) vol. 38, No. 20, pp. 3933–3940.

Newman, et al., *Current Medicinal Chem.* (1998) vol. 5, No. 4, pp. 305–319.

Newman, et al., *J. Med. Chem.* (1994) vol. 37, No. 15, pp. 2258–2261.

Riley et al., *J. Med. Chem.* (1979) pp. 1167–1171.

Van Eeken, et al., *Arch. Int. Pharmacodyn* (Netherlands) (1966) vol. 22, No. 10, vol. 159, No. 1, pp. 240–249.

Cesati, et al., *J. Labelled Cpd. Radiopharm*, (1999) vol. 42, Suppl. j, pp. S150–S152.

Fang, et al., *J. Labelled Cpd. Radiopharm.* (1999) vol. 42, Suppl. i, pp. S336–S338.

Hoepping, et al., Universitat Marburg, Pachbereich Kemchemie, (1997) pp. 33–36.

Hoepping, et al., *Bioorganic & Medicinal Chem.* (1998) vol. 6, pp. 1663–1672.

Hoepping, et al., *Bioorganic & Medicinal Chem.* (1996) vol. 6, No. 23, pp. 2871–2874.

Hoepping, et al., *J. Med. Chem.* (1998) vol. 41, No. 23, pp. 4429–4432.

Madras, et al., *Synapse* (1996) vol. 22, pp. 239–246.

Meegalla, et a l., *J. Med. Chem.* (1997) vol. 40, No. 1, pp. 9–17.

Meltzer, et al., *J. Med. Chem.* (1997) vol. 40, No. 12, pp. 1835–1844.

Meltzer, et al., *J. Med. Chem.* (1993) vol. 36, No. 7 pp. 855–862.

Meltzer, et al., *Med. Chem. Research* (1998) pp. 12–34.

Meegalla, et al., *Bioconjugate Chem.* (1996) vol. 7, No. 4, pp. 421–429.

Fischman, et al., *J. Nuclear Med.* vol. 40, No. 5 Supplement, p. 262P.

Mozley, et al., *J. Nuclear Med.* (1995) vol. 36, No. 5, p. 32P.

Myers, et al., *J. Nuclear Med.* (1995) vol. 36, No. 5, p. 124P.

Madras et al., Technepine: A high–Affinity $^{99m}$Technetium probe to label the Dopamine Transporter in Brain by SPECT Imaging; Synapse, (1996), vol. 24, pp. 340–348.

Goulet et al., Synapse (2001), vol. 42, pp. 129–140.

Meltzer et al., 2–Carbomethoxy–3–aryl–8–bicyclo [3.2.1.] octanes: Potent Non–Nitrogen Inhibitors of monoamine Transporters, J. Med. Chem., (2000), vol. 43, No. 16, pp. 2982–2991.

Meltzer, Journal of Medicinal Chemistry (1997), vol. 40, No. 17, pp. 2661–2673.

Scheme 1. Synthesis of 2-carbomethoxy-3-arylbicyclo[3.2.1]octanes

Ar = a. 3,4-Cl$_2$C$_6$H$_3$   b. 2-Naphthyl   c. 4-FC$_6$H$_4$   d. C$_6$H$_5$

Reagents: i) H$_2$SO$_4$; ii) LDA/THF, CNCOOCH$_3$; iii) NaN(TMS)$_2$, PhNTf$_2$; iv) ArB(OH)$_2$, Pd$_2$(dba)$_3$; v) SmI$_2$, CH$_3$OH Scheme 2 Synthesis of 3-aryl-8-oxabicyclo[3.2.1]octanes

| R | a | b | c | d | e | f | g | h |
|---|---|---|---|---|---|---|---|---|
| 15,16,17 | H R/S | F R/S | Cl R/S | Br R/S | I R/S | 3,4-$Cl_2$ R/S | 3,4-$Cl_2$ 1R | 3,4-$Cl_2$ 1S |

| R | i | j | k | l |
|---|---|---|---|---|
| 15,16,17 | CHO R/S | $CH(CH_3)_2$ R/S | $C(CH_3)=CH_2$ R/S | $C{\equiv}CCH_3$ R/S |

Reagents: i) $TiCl_4$. ii) $Na(TMS)_2N$, $Ph(Tf)_2N$, THF, -78°C. iii) $ArB(OH)_2$, $Pd_2dba_3$, $Na_2CO_3$, LiCl. iv) $SmI_2$, Methanol, -78°C.

Scheme 3  Resolution of keto ester 3

Reagents: i) Na(TMS)₂N, (S)-Camphanic chloride or (R)-Camphanic chloride, THF, -78°C. ii) Hexane / CH₂Cl₂ (2:1), 0°C.
iii) LiOH, THF, MeOH, H₂O.

SEROTONIN TRANSPORT INHIBITORS

This application is a continuation 10/097,062, filed on Mar. 13, 2002, which is a continuation of 09/875,523, filed on Jun. 6, 2001, which is a continuation of 09/671,534, filed Sep. 27, 2000, which is a division of Ser. No. 09/314,441 filed May, 19, 1999, which is a division of Ser. No. 08/893,921 filed Jul. 11, 1997, now U.S. Pat. No. 5,948,933.

This application claims the benefit of provisional application No. 60/328,523 filed Oct. 10, 2001.

STATEMENT OF GOVERNMENT SUPPORT

This invention is supported by NIH Grant Nos. RR00168, DA78081, DA11542, DA00304, DA11558 and DA06303 and the government has certain rights to the invention.

FIELD OF THE INVENTION

The present invention relates to compounds that inhibit 5-hydroxytryptamine reuptake and the use of those compounds on diseases mediated by 5HT receptors. Compounds that provide such inhibition can be useful, for example, as therapeutic anti-depressants.

BACKGROUND OF THE INVENTION

Serotonin (5-hydroxytryptamine) neurotransmission is regulated and terminated by active transport via the serotonin transporter (SERT). The SERT is member of a large superfamily of sodium/chloride dependent transporters that carry biogenic amines and other biologically active substrates to the interior of cells (Amara S G, Kuhar M J. 1993. 16:73–93; Blakely R D, et al., 1994. J Exp Biol 196:263–281). Structurally related to dopamine and norepinephrine transporters (Nelson N. 1998. J Neurochem 71:1785–1803), the SERT is the primary site of action of diverse antidepressant drugs, ranging from tricyclics such as imipramine and amitriptyline, to serotonin selective reuptake inhibitors (SSRI's) such as citalopram, fluoxetine and sertraline.

Antidepressant drugs delay the removal of extracellular serotonin from the synapse by blocking serotonin transport, thereby prolonging the duration of serotonin receptor activity. The increased availability of serotonin triggers a cascade of neuroadaptive processes, which produces symptom relief after two to four weeks. Presently known antidepressants also produce certain side effects and may selectively alleviate specific symptoms of depression (Nestler E J. 1998. Biol Psychiatry 44:526–533). Thus, it is desirable to develop novel antidepressants. The majority of clinically approved drugs to treat depression or obsessive-compulsive disorder are high affinity inhibitors of serotonin and/or norepinephrine transport. Of these transporter inhibitors, none are tropane analogs, they display low affinity for the dopamine transporter (DAT), and all contain an amine nitrogen in their structure.

Over the past decade, a wide array of tropane analogs with high affinity for the monoamine transporters have been synthesized in a program to develop cocaine medications (Madras B K, et al., 1990. Pharmacol Biochem Behav 35:949–953; Madras B K, et al., 1996. Synapse 24:340–348; Carroll F I, et al., 1992. J Med Chem 35:2497–2500; Meltzer P C, et al., 1994. J Med Chem 37:2001–2010; Kozikowski A P, et al., 1995. J Med Chem 38:3086–3093; Lomenzo S A, et al., 1997. J Med Chem 40:4406–4414; Davies H M, et al., 1994. J Med Chem 37:1262–1268). The majority of these compounds target the dopamine transporter and have not been considered candidate medications for depression because of stimulant or abuse liability concerns (Reith M E, et al., 1986. Biochem Pharmacol 35:1123–1129; Ritz M C, et al., 1987. Science 237:1219–1223; Madras B K, et al., 1989. J Pharmacol Exp Ther 251:131–141; Bergman J, et al., 1989. J Pharmacol Exp Ther 251:150–155). Tropane analogs selective for the serotonin over the dopamine transporter have been reported. (Blough B E, et al., 1996. J Med Chem 39:4027–4035; Blough B E, et al., 1997. J Med Chem 40:3861–3864; Smith M P, et al., 1998. J Am Chem Soc 1201:9072–9075; Davies, H M, et al., 1996. J Med Chem 39:2554–2558.

Psychotherapeutics drugs, including antidepressants, all incorporate an amine nitrogen into the structure. In fact, antidepressants presently used have an aromatic ring(s) and an amine nitrogen. Although the aromatic ring is an indispensable component of most drugs acting on biogenic amine receptors or transporters, we previously demonstrated that an amine nitrogen is not necessary for compounds to bind to or block the dopamine transporter (Madras B K, et al., 1996. Synapse 24:340–348; Meltzer P C, et al., 1997. J Med Chem 40:2661–2673; Meltzer P C, et al., 1999. Bioorg Med Chem Lett 9:857–862; Meltzer P C, 2000. J Med Chem 43:2982–2991). Biological activity of these compounds was retained if the amine nitrogen was replaced either by an oxygen (oxa) atom or a carbon (carba) atom (Madras B K, et al., 1996. Synapse 24:340–348; Madras B K, et al., 1998. Soc for Neurosci Abst 24:113.11, 278p; Madras B K, et al., Addiction Biology 5:351–359, 2000; Meltzer P C, 2000. J Med Chem 43:2982–2991).

It would be desirable to have high affinity non-amines with selectivity for the serotonin transporter and compounds that inhibit the transport of serotonin.

SUMMARY OF THE INVENTION

The present invention relates to the discovery that tropane compounds lacking an amine group show surprisingly effective results in treating certain neuropsychiatric disorders related to serotonin transport.

Compounds that are useful as therapeutic agents in the methods of the present invention include non-amine tropane compounds represented by the following general structural formula:

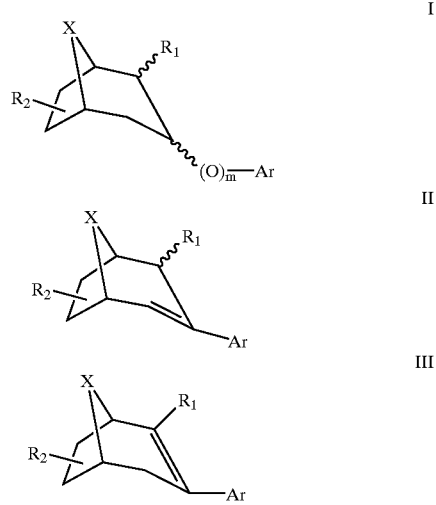

wherein:
R$_1$=COOCH$_3$, COR$_3$, lower alkyl, lower alkenyl, lower alkynyl, CONHR$_4$, or COR$_6$;

$R_2=$ is a 6α, 6β, 7α or 7β substituent, which can be selected from H, OH, $OR_3$, F, Cl, Br, and $NHR_3$;

$X=CH_2$, CHY, $CYY_1$, CO, O, S; SO, $SO_2$, or $C=CX_1Y$ with the C, O or S atom being a member of the ring;

$X_1=NR_3$, $CH_2$, CHY, $CYY_1$ CO, O, S; SO, $SO_2$, or $NSO_2R_3$;

$R_3=$H, $(CH_2)_nC_6H_4Y$, $C_6H_4Y$, $CHCH_2$, lower alkyl, lower alkenyl or lower alkynyl;

Y and $Y_1=$H, Br, Cl, I, F, OH, $OCH_3$, $CF_3$, $NO_2$, $NH_2$, CN, $NHCOCH_3$, $N(CH_3)_2$, $(CH_2)_nCH_3$, $COCH_3$, or $C(CH_3)_3$;

$R_4=CH_3$, $CH_2CH_3$, or $CH_3SO_2$;

$R_6=$morpholinyl or piperidinyl;

$Ar=$phenyl-$R_5$, naphthyl-$R_5$, anthracenyl-$R_5$, phenanthrenyl-$R_5$, or diphenylmethoxy-$R_5$;

$R_5=$Br, Cl, I, F, OH, $OCH_3$, $CF_3$, $NO_2$, $NH_2$, CN, $NHCOCH_3$, $N(CH_3)_2$, $(CH_2)_nCH_3$, $COCH_3$, $C(CH_3)_3$ where n=0–6, 4-F, 4-Cl, 4-I, 2-F, 2-Cl 2-I, 3-F, 3-Cl 3-I, 3,4-diCl, 3,4-diOH, 3,4-diOAc, 3,4-di$OCH_3$, 3-OH-4-Cl, 3-OH-4-F, 3-Cl-4-OH, 3-F-4-OH, lower alkyl, lower alkoxy, lower alkenyl, lower alkynyl, CO(lower alkyl), or CO(lower alkoxy);

m=0 or 1; and n=0, 1, 2, 3, 4 or 5.

Preferred compounds have a SERT/DAT selectivity ratio of at least about 3. Other embodiments have a SERT/DAT selectivity ratio of at least about 8 and other preferably at least about 50.

The invention also relates to compounds shown above that have a potency ($K_i$), or $IC_{50}$, at the SERT of less than about 500 nM, preferably less than about 100 nM. In certain preferred embodiments the compounds have a $K_i$ at the SERT less than about 50 nM, preferably less than about 25 nM and more preferably less than about 15 nM.

Especially preferred compounds have a SERT/DAT selectivity ratio of at least about 3 and an $IC_{50}$ at the SERT of less than about 500 nM.

The substituents at the 2 and 3 position of the ring can be α- or β-. Thus, the compounds include compounds in the boat and chair conformation. Although $R_1$ is illustrated in the 2-position, it should be recognized that substitution at the 4-position is also included and the position is dependent on the numbering of the tropane ring. The compounds of the present invention can be racemic, pure R-enantiomers, or pure S-enantiomers. Thus, the structural formulas illustrated herein are intended to represent each enantiomer and diastereomer of the illustrated compound.

The term "lower alkyl" when used herein designates aliphatic saturated branched or straight chain hydrocarbon monovalent substituents containing from 1 to about 8 carbon atoms such as methyl, ethyl, isopropyl, n-propyl, n-butyl, $(CH_2)_nCH_3$, $C(CH_3)_3$; etc., more preferably 1 to 4 carbons. The term "lower alkoxy" designates lower alkoxy substituents containing from 1 to about 8 carbon atoms such as methoxy, ethoxy, isopropoxy, etc., more preferably 1 to 4 carbon atoms.

The term "lower alkenyl" when used herein designates aliphatic unsaturated branched or straight chain vinyl hydrocarbon substituents containing from 2 to about 8 carbon atoms such as allyl, etc., more preferably 2 to 4 carbons. The term "lower alkynyl" designates lower alkynyl substituents containing from 2 to about 8 carbon atoms, more preferably 2 to 4 carbon atoms such as, for example, propyne, butyne, etc.

The terms substituted lower alkyl, substituted lower alkoxy, substituted lower alkenyl and substituted lower alkynyl, when used herein, include corresponding alkyl, alkoxy, alkenyl or alkynyl groups substituted with halide, hydroxy, carboxylic acid, or carboxamide groups, etc. such as, for example, —$CH_2OH$, —$CH_2CH_2COOH$, —$CH_2CONH_2$, —$OCH_2CH_2OH$, —$OCH_2COOH$, —$OCH_2CH_2CONH_2$, etc. As used herein, the terms lower alkyl, lower alkoxy, lower alkenyl and lower alkynyl are meant to include where practical substituted such groups as described above.

When X contains a carbon atom as the ring member, reference to X is sometimes made herein as a carbon group. Thus, when X is a carbon group, as that phrase is used herein, it means that a carbon atom is a ring member at the X position (i.e., the 8-position).

The present invention also relates to therapeutic uses of non-amine tropane analogs. More specifically, the invention relates to methods of treating patients having SERT related disorders, comprising administering to the patient a serotonin reuptake inhibiting amount of a non-amine compound. Such diseases include, but are not limited to, e.g., depression, anxiety, eating disorders and obsessive compulsive disorders and other. The methods specifically include therapies for treating depression.

More specifically, the invention relates to the use of non-amine tropane compounds, as described further below, for the treatment of these diseases. Particularly preferred compounds comprise the compounds shown in FIG. 1 and described herein.

The present invention provides pharmaceutical therapeutic compositions comprising the compounds formulated in a pharmaceutically acceptable carrier for use in the present methods.

Further, the invention provides a method for inhibiting 5-hydroxytryptamine (Serotonin) reuptake of a monoamine transporter by contacting the monoamine transporter with a 5-hydroxy-tryptamine reuptake inhibiting (5-HT inhibiting) amount of a non-amine tropane compound. Inhibition of 5-hydroxy-tryptamine reuptake of a serotonin transporter in a mammal is provided in accord with the present invention by administering to the mammal a 5-HT inhibiting amount of a non-amine tropane compound in a pharmaceutically acceptable carrier.

DETAILED DESCRIPTION OF THE INVENTION

Figure 1:
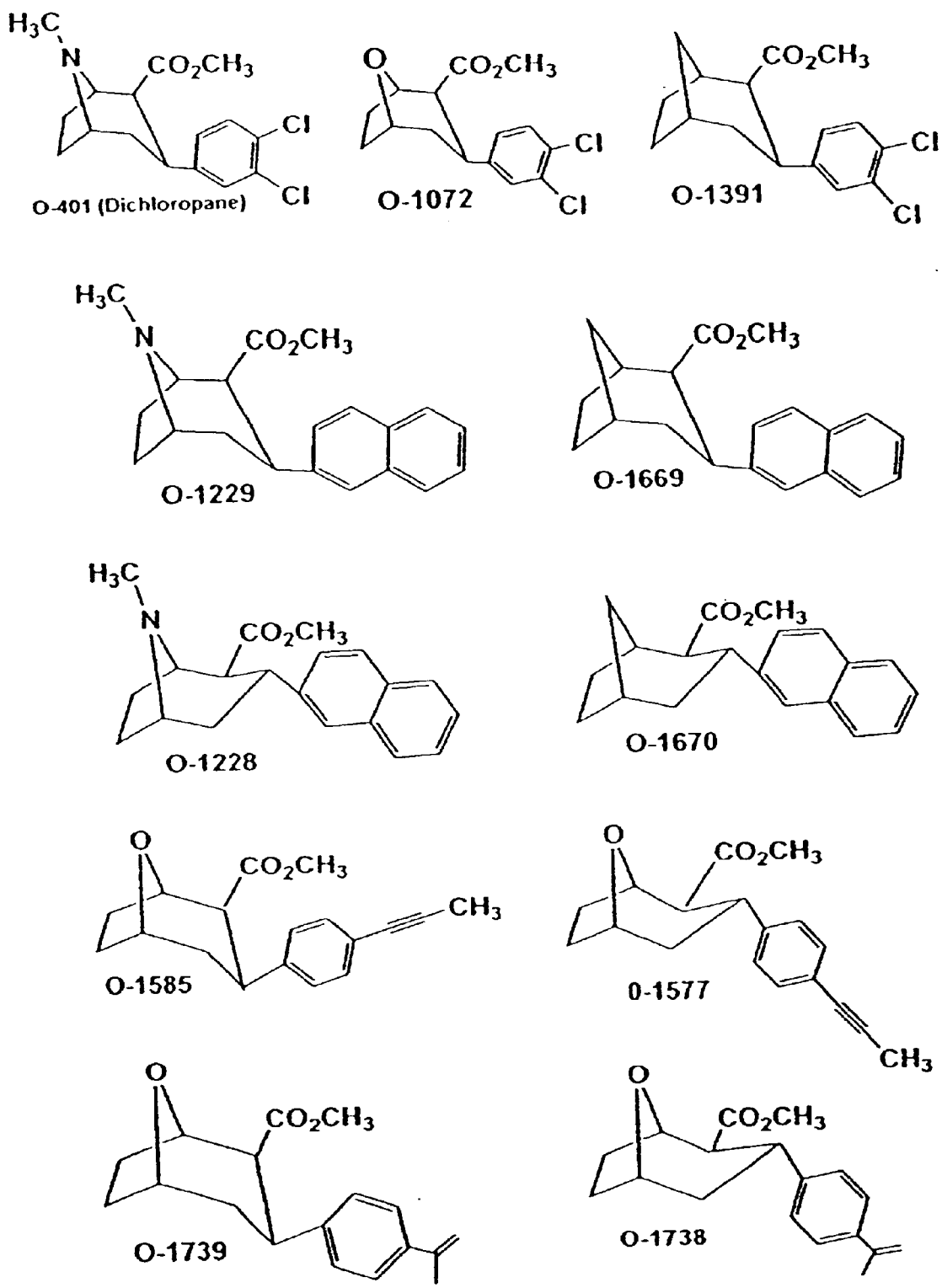
FIG. 1 shows the chemical structure of novel amines and novel non-amines, all of which share a tropane backbone.

The present invention relates to the use of high affinity serotonin transport inhibitors, designated non-amines, that contain no amine nitrogen in their structure. These tropane analogs, in which the amine nitrogen is replaced by an oxa or carba atom (Madras B K, et al., 1996. Synapse 24:340–348; Meltzer P C, et al., 1997. J Med Chem 40:2661–2673 Meltzer P C, et al., 1997. J Med Chem 40:2661–2673; Meltzer P C, et al., 1999. Bioorg Med Chem Lett 9:857–862; Meltzer P C, 2000. J Med Chem 43:2982–2991), are generally described in U.S. Pat. No. 5,948,933, which issued Sep. 7, 1999.

The present invention relates to the use of specific compounds that bind to the SERT to treat neuropsychiatric disorders, wherein the compound is a non-amine and blocks serotonin transport. Certain preferred compounds have a high selectivity for the SERT versus the DAT as described herein.

The compounds used in the methods of the present invention inhibit serotonin uptake and have the following structural formulas:

Compounds that are useful as therapeutic agents in the methods of the present invention include compounds represented by the following general structural formula:

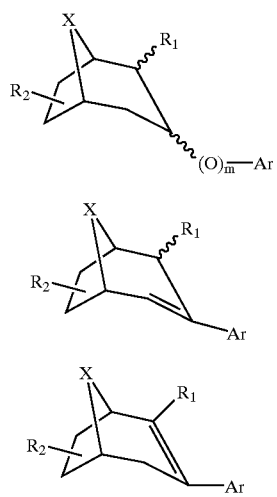

wherein:

$R_1$=COOCH$_3$, COR$_3$, lower alkyl, lower alkenyl, lower alkynyl, CONHR$_4$, or COR$_6$;

$R_2$=is a 6α, 6β, 7α or 7β substituent, which can be selected from H, OH, OR$_3$, F, Cl, Br, and NHR$_3$;

X=CH$_2$, CHY, CYY$_1$, CO, O, S; SO, SO$_2$, or C=CX$_1$Y with the C, O or S atom being a member of the ring;

X$_1$=NR$_3$, CH$_2$, CHY, CYY$_1$ CO, O, S; SO, SO$_2$, or NSO$_2$R$_3$;

$R_3$=H, (CH$_2$)$_n$C$_6$H$_4$Y, C$_6$H$_4$Y, CHCH$_2$, lower alkyl, lower alkenyl or lower alkynyl;

Y and Y$_1$=H, Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, or C(CH$_3$)$_3$;

$R_4$=CH$_3$, CH$_2$CH$_3$, or CH$_3$SO$_2$;

$R_6$=morpholinyl or piperidinyl;

Ar=phenyl-R$_5$, naphthyl-R$_5$, anthracenyl-R$_5$, phenanthrenyl-R$_5$, or diphenylmethoxy-R$_5$;

$R_5$=Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, C(CH$_3$)$_3$ where n=0–6, 4-F, 4-Cl, 4-I, 2-F, 2-Cl, 2-I, 3-F, 3Cl, 3-I, 3,4-diCl, 3,4-diOH, 3,4-diOAc, 3,4-diOCH$_3$, 3-OH-4-Cl, 3-OH-4-F, 3-Cl-4-OH, 3-F-4-OH, lower alkyl, lower alkoxy, lower alkenyl, lower alkynyl, CO(lower alkyl), or CO(lower alkoxy);

m=0 or 1; and n=0, 1, 2, 3, 4 or 5.

Preferred compounds have a SERT/DAT selectivity ratio of at least about 3. Other embodiments have a SERT/DAT selectivity ratio of at least about 8 and other preferably at least about 50.

The invention also relates to compounds shown above that have a potency (K$_i$), or IC$_{50}$, at the SERT of less than about 500 nM, preferably less than about 100 nM. In certain preferred embodiments the compounds have a K$_i$ at the SERT more less than about 50 nM, preferably less than about 25 nM and more preferably less than about 15 nM.

Especially preferred compounds have a SERT/DAT selectivity ratio of at least about 3 and a potency (K$_i$) at the SERT of less than about 500 nM.

In another preferred embodiment of the present invention, preferred 8-oxatropanes and 8-carbatropanes include those having alkenyl and alkynyl groups on the 3-aryl ring, particularly of the 2-COOCH$_3$ tropanes, to enhance potency at the SERT. Particularly preferred examples of such compounds have the following formula:

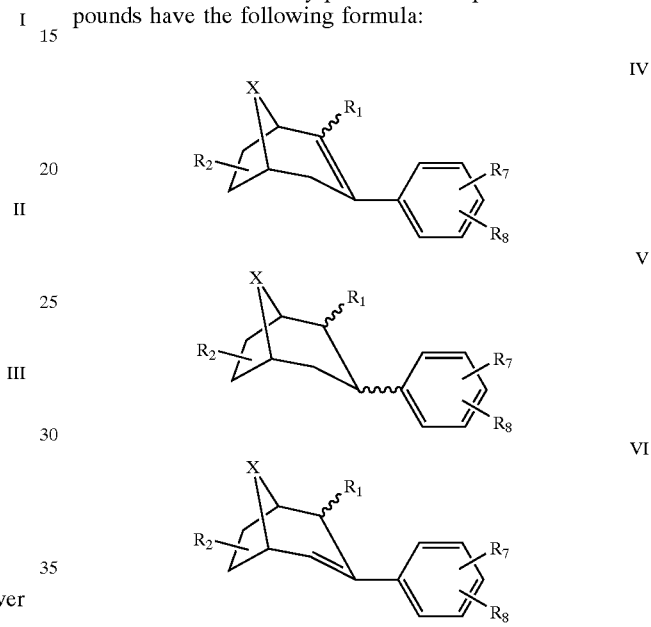

where X is an oxygen or a carbon group such as, for example, CH$_2$, CHY, CYY$_1$, CO, or C=CX$_1$Y where X$_1$, Y and Y$_1$ are defined above, and R$_7$ is a lower alkenyl or lower alkynyl group having from about 2 to about 8 carbon atoms. Particularly preferred lower alkenyl and lower alkynyl groups are ethenyl, propenyl, butenyl, propynyl, butynyl and methylpropynyl. R$_8$ is H or Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, C(CH$_3$)$_3$ where n=0–6.

The compounds are prepared as racemates and individual enantiomers. These compounds can be prepared either as free bases or as pharmacologically active salts thereof such as hydrochloride, tartrate, sulfate, naphthalene-1,5-disulfonate or the like. In certain preferred compounds, when R$_2$ is not H, i.e., the compounds are 6 or 7 substituted compounds, the compounds have the 1 S conformation. In other preferred compounds, when R$_2$ is H, the compounds preferably have the R conformation.

FIG. 1 shows the chemical structure of amines and non-amines, all of which share a tropane backbone. The dichlorophenyl substituted non-amines are derived from an amine (aza, O-401) in which the amine nitrogen is replaced with a oxygen (oxa, O-1072) or carbon (carba, O-1391). The naphthyl substituted non-amines are derived from diastereomeric amines (aza, O-1229, O-1228) in which the amine nitrogen is replaced with a carbon (carba, O-1669, O-1670). Compounds O-1585 and O-1577 are propynylphenyl derivatives. O-1738 and O-1739 are isopropenylphenyl analogs of tropanes.

Figure 2:
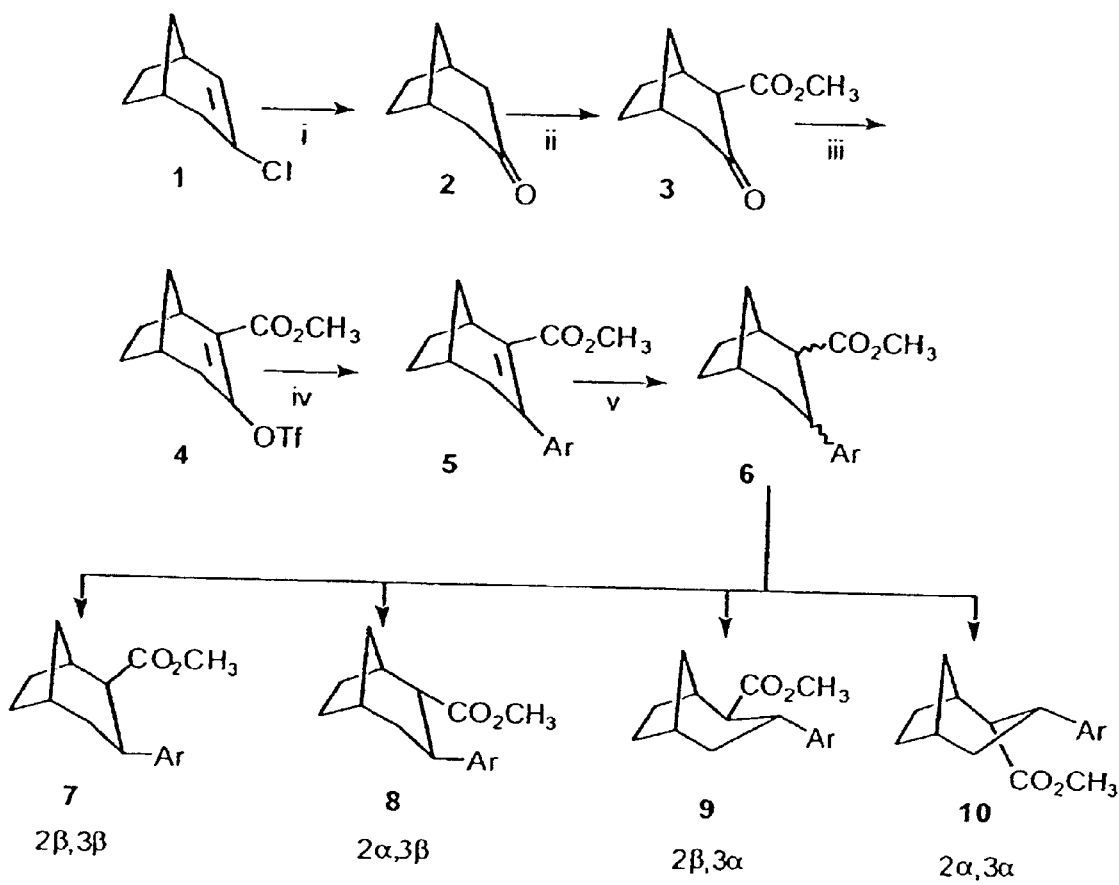
FIG. 2 shows reaction Scheme 1 for the synthesis of 2-carbomethoxy-3-arylbicyclo(3.2.1)octanes.
Figure 3:
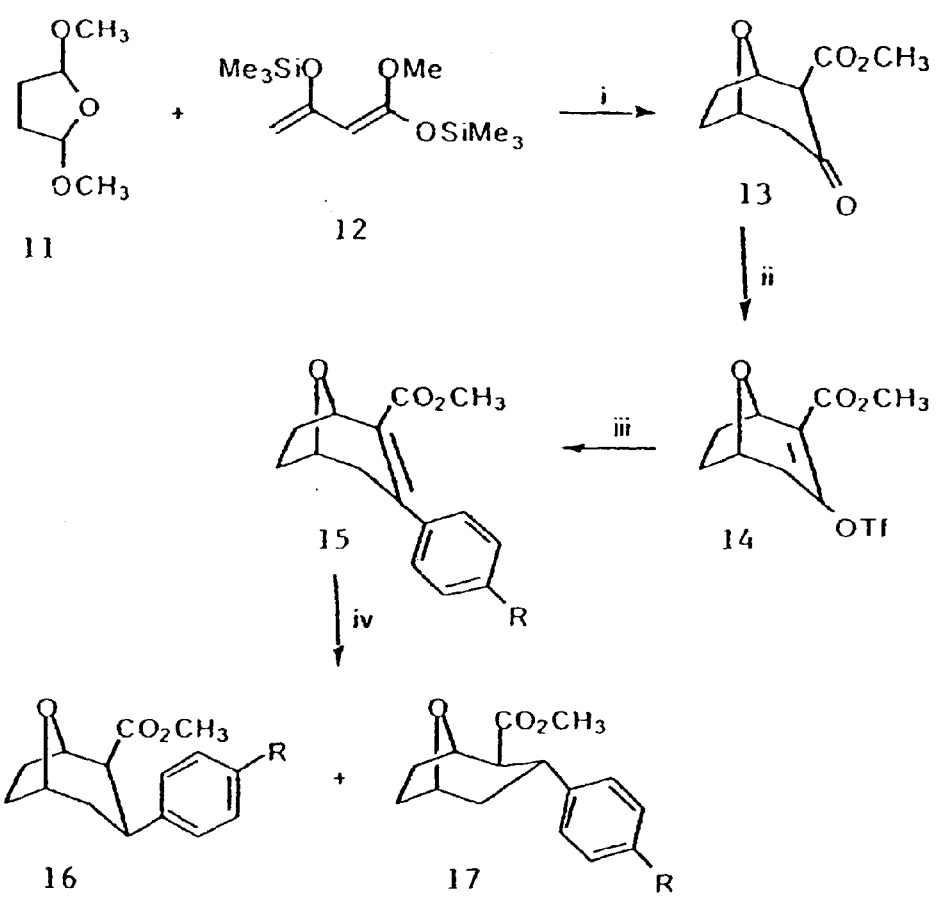
FIG. 3 shows reaction Scheme 2 for the synthesis of 3-aryl-8-oxabicyclo(3.2.1)octanes.
Figure 4:
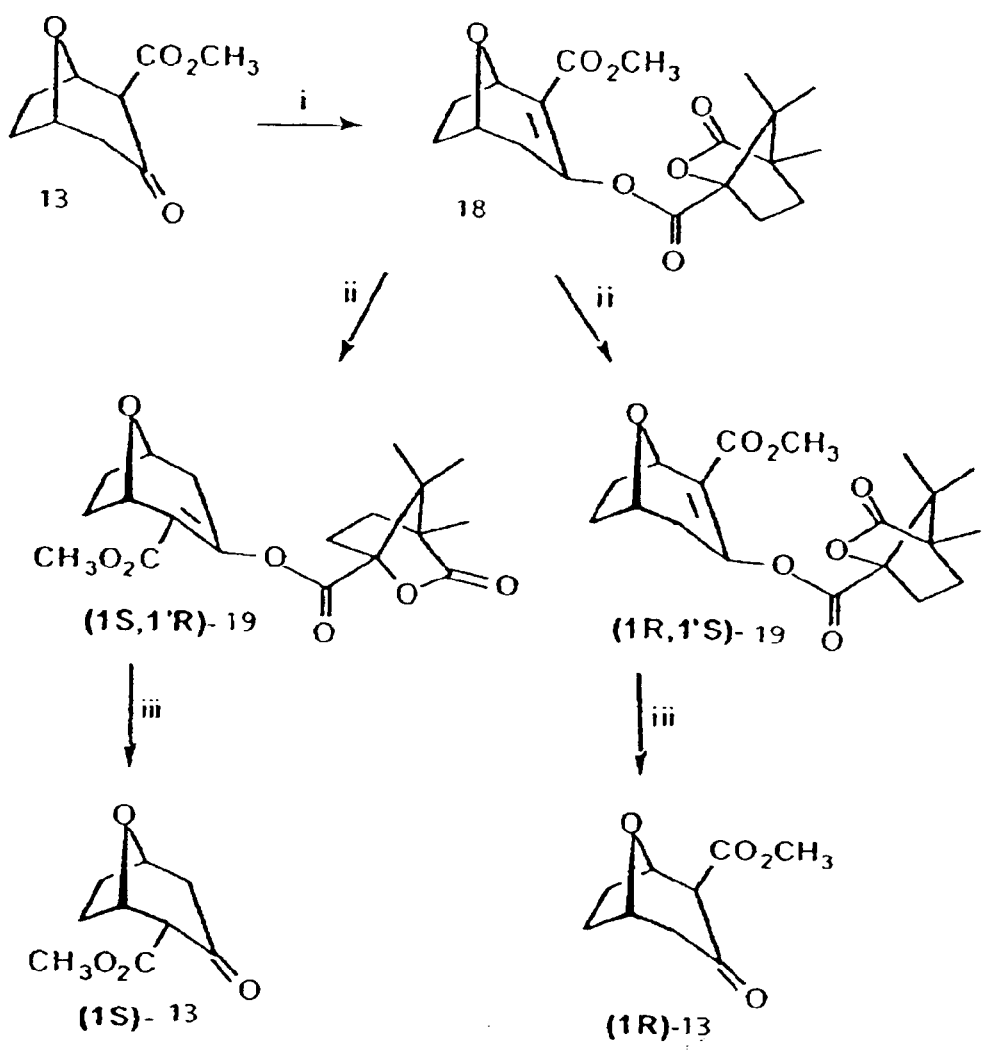
FIG. 4 shows reaction Scheme 3 for the resolution of keto ester.

Examples of preferred compounds for use in the methods of the repent invention include, but are not limited to: O-1229: N-methyl-2β-carbomethoxy-3β(2'-naphthyl)-8-azabicyclo(3.2.1)octane; O-1228: N-methyl-2β-carbomethoxy-3-(2'-naphthyl)-8-azabicyclo(3.2.1)octane; O-1072: 2-β-carbomethoxy-3-β-(3,4-dichlorophenyl)-8-oxabicyclo(3.2.1)octane; O-1391: 2-β-carbomethoxy-3-β-(3,4-dichlorophenyl)bicyclo(3.2.1)octane; O-1577: 2β-carbomethoxy-3β-(4'-propynylphenyl))-8-oxabicyclo(3.2.1)octane; O-1585: 2β-carbomethoxy-3α-(4'-propynylphenyl)-8-oxabicyclo(3.2.1)octane; O-1669: 2β-carbomethoxy-3β-(2-naphthyl)-8-bicyclo(3.2.1)octane; O-1670: 2β-carbomethoxy-3α-(2-naphthyl)-8-bicyclo(3.2.1)octane; O-1738: 2β-carbomethoxy-3α-(4-isopropenylphenyl)-8-oxabicyclo(3.2.1)octane; O-1739: 2β-carbomethoxy-3β-(4-isopropenylphenyl)-8-oxabicyclo(3.2.1)octane; O-1809: 2β-carbomethoxy-3β-(4-isopropenylphenyl)-8-oxabicyclo(3.2.1)octane. The synthesis of these compounds and other is shown in FIGS. 2–4 and described below in the Examples.

The compounds described herein provide a broad array of molecules including compounds that bind to the SERT with very high affinity. Selectivity for inhibition of the SERT versus the DAT is another property of tropanes of considerable relevance for development of medications for treating SERT related disorders. Preferred compounds for the present methods exhibit the desired target:non-target (SERT:DAT) specificity. The serotonin transporter is detectable in the striatum, the brain region with the highest density of dopamine neurons and in brain regions surrounding the striatum. It is necessary to determine whether the candidate compound is more potent at the serotonin than the dopamine transporter. If more selective (e.g., >10-fold), the compound will provide effective treatment modality for the SERT. Therefore, a measure of probe affinity of the serotonin transport is conducted by assays paralleling the dopamine transporter assays. As described below, ($^3$H)Citalopram is used to radiolabel binding sites on the serotonin transporter and competition studies are conducted with the candidate compound at various concentrations in order to generate an $IC_{50}$ value.

Whether oxa or carba based, non-amines of the present invention bound to ($^3$H)citalopram labeled sites and blocked ($^3$H)serotonin transport in the low nanomolar range. These results are comparable or better than those of some conventional antidepressants. For example, O-1809, is 99-fold more selective for the serotonin transporter over the dopamine transporter.

The non-amines had varying affinities and serotonin:dopamine transporter (SERT/DAT) selectivities, as measured in monkey brain tissue (Table 2). As described above, preferred compounds for use in the methods of the present invention have a SERT/DAT selectivity ratio of at least about 3. Other embodiments have a SERT/DAT selectivity ratio of at least about 8 and other preferably at least about 50. Examples of preferred serotonin transporter-selective non-amines include O-1809, O-1739, O-1577, O-1738 and O-1585.

Affinity, i.e., binding to the SERT, is another characteristic that is useful for selecting useful compounds. The oxa (O-1072) or carba (O-1391) analogs of O-401, a high affinity amine that is relatively non-selective for the dopamine over the serotonin transporter, displayed similar high affinity and non-selective binding to the dopamine and serotonin transporters. The compounds of the present invention have an affinity, also known as potency, $IC_{50}$ or $K_i$, at the SERT of less than about 500 nM, preferably less than about 50 nM.

In certain preferred embodiments the compounds have a $K_i$ at the SERT more preferably less than about 25 nM and more preferably less than about 15 nM.

For example, the non-amines O-1072, O-1391, O-1809, O-1669, O-1739 blocked ($^3$H)serotonin transport in the low nanomolar range, comparable to the potencies of the conventional amine antidepressants, imipramine, fluoxetine and amitriptyline (see Tables 1–4). Amine antidepressants displayed lower potencies for blocking serotonin transport than for binding to ($^3$H)citalopram labeled sites. Initially reported in 1997 (Owens M J, et al., 1997. J Pharmacol Exp Ther 283:1305–1322), this discrepancy between drug binding potencies and blockade of serotonin transport was not observed if ($^{125}$I)RTI-55 was used to label the serotonin transporter (Eshleman A J, et al., 1999. J Pharmacol Exp Ther 289:877–885), but was even more prominent with ($^3$H)paroxetine as a probe for the serotonin transporter (Kuhar M J, et al., 1999. Drug Alcohol Depend 56:9–15). The potencies of non-amines for blocking the serotonin transporter are comparable to conventional and widely used amine-based antidepressants.

Using the combination of selectivity (SERT/DAT ratio) and potency ($IC_{50}$) information for these compounds, one of ordinary skill in the art can readily select the appropriate compound for the desired application, e.g., treatment of SERT related disorders.

Substituents on the aromatic ring of non-amines enhanced SERT affinities by 10 to 1,000-fold. The increases were greater than those observed with corresponding monoamines. Certain preferred compounds for use in the present invention are non-amines with substituted aromatic rings at the 3 position.

The compounds and pharmaceutical preparations of the present invention can be used to inhibit the serotonin reuptake by the serotonin transporter. The pharmaceutical compositions, preferably comprise the compounds of the present invention in a pharmaceutically acceptable carrier. Pharmaceutically acceptable carriers are well known to those skilled in the art. An exemplary pharmaceutical composition is a therapeutically effective amount of a compound of the invention optionally included in a pharmaceutically-acceptable and compatible carrier. The term "pharmaceutically-acceptable and compatible carrier" as used herein, and described more fully below, refers to e.g., one or more compatible solid or liquid filler diluents or encapsulating substances that are suitable for administration to a human or other animal. The route of administration can be varied but is principally selected from intravenous, nasal and oral routes. For parenteral administration, e.g., it will typically be injected in a sterile aqueous or non-aqueous solution, suspension or emulsion in association with a pharmaceutically-acceptable parenteral carrier such as physiological saline.

The term "therapeutically-effective amount" is that amount of the present pharmaceutical compositions which produces a desired result or exerts a desired influence on the particular condition being treated. Various concentrations may be used in preparing compositions incorporating the same ingredient to provide for variations in the age of the patient to be treated, the severity of the condition, the duration of the treatment and the mode of administration. An effective dose of the compound is administered to a patient based on $IC_{50}$ values determined in vitro. The route of administration can be varied but is principally selected from intravenous, nasal and oral routes. The effective dose can vary depending upon the mode of administration as is well known in the art.

The term "compatible", as used herein, means that the components of the pharmaceutical compositions are capable of being commingled with the compounds of the present invention, and with each other, in a manner such that there is no interaction that would substantially impair the desired pharmaceutical efficacy.

The dose of the pharmaceutical compositions of the invention will vary depending on the subject and upon particular route of administration used. The pharmaceutical compositions can also be administered to a subject according to a variety of well-characterized protocols. In a preferred embodiment, the pharmaceutical composition is a liquid composition in pyrogen-free, sterilized container or vial. The container can be unit dose or multidose.

This invention will be illustrated further by the following examples. These examples are not intended to limit the scope of the claimed invention in any manner. The Examples provide suitable methods for preparing compounds of the present invention. However, those skilled in the art may make compounds of the present invention by any other suitable means. As is well known to those skilled in the art, other substituents can be provided for the illustrated compounds by suitable modification of the reactants.

EXAMPLES

Materials

The following drugs were obtained from the sources listed: (−)cocaine hydrochloride (National Institute on Drug Abuse, Bethesda, Md.); mazindol base (Sandoz Inc., East Hanover, N.J.); citalopram hydrobromide and talsupram hydrochloride (Lundbeck A/S, Copenhagen, Denmark); dopamine hydrochloride, (−)-norepinephrine bitartrate and serotonin creatinine sulfate (Sigma Chemical Co., St. Louis, Mo.); RTI-55 methyl ester tartrate (F. Ivy Carroll, Research Triangle Institute, Research Triangle Park, N.C.); imipramine (Ciba Pharmaceuticals, Summit, N.J.); sertraline (McNeil Pharmaceutical, Raritan, N.J.); fluoxetine hydrochloride (Eli Lilly, Indianapolis, Ind. and Sigma/Research Biochemicals, Natick, Mass.); amitriptyline and desipramine (Merck Sharp and Dohme Ltd., Rahway, N.J.). Amine and non-amine drugs, designated with the prefix O-, were synthesized by Organix Inc., (Woburn, Mass.) in accordance with the methods described in U.S. Pat. No. 5,948,933, Meltzer, et al, J. Med. Chem. 40, 2661–2673, 1997 and Reference: Meltzer et al, J. Med. Chem. 43, 2982–2991, 2000. Examples of preferred structures are shown in FIG. 1.

Chemical Synthesis

A. Synthesis of 2-Carbomethoxy-3-Arylbicyclo (3.2.1) Octanes

Scheme 1 (FIG. 2) shows the Synthesis of 2-carbomethoxy-3-arylbicyclo (3.2.1)octanes. All compounds are racemates (1R/1S). NMR spectra were recorded in $CDCl_3$ on a JEOL 300 NMR spectrometer operating at 300.53 MHz for $^1H$, and 75.58 MHz for $^{13}C$. TMS was used as internal standard. Melting points are uncorrected and were measured on a Gallenkamp melting point apparatus. Thin layer chromatography (TLC) was carried out on Baker Si250F plates. Visualization was accomplished with either UV exposure or treatment with phosphomolybdic acid (PMA). Flash chromatography was carried out on Baker Silica Gel 40 mM. Elemental analyses were performed by Atlantic Microlab, Atlanta, Ga. All reactions were conducted under an inert ($N_2$) atmosphere. ($^3H$)WIN 35,428 (2β-carbomethoxy-3 β-(4-fluorophenyl)-N-($^3H$)methyltropane, 79.4–87.0 Ci/mmol) and ($^3H$)citalopram (86.8 Ci/mmol) were purchased from DuPont-New England Nuclear (Boston, Mass.). A Beckman 1801 scintillation counter was used for scintillation spectrometry. 0.1% Bovine serum albumin was purchased from Sigma Chemicals. (R)-(−)-Cocaine hydrochloride for the pharmacological studies was donated by the National Institute on Drug Abuse (NIDA).

2-Carbomethoxy-bicyclo(3.2.1)octan-3-one (3)

To bicyclo(3.2.1)octan-3-one, $2^{27}$ (6.42 g, 51.7 mmol) in THF (75 mL), lithium diisopropyl amide (31 mL, 62 mmol) in THF (125 mL) was added dropwise at −78° C. The mixture was stirred at −78° C. for 1 h and methyl cyanoformate (4.9 mL, 62 mmol) was added. The cooling bath was removed and the reaction allowed to warm to room temperature. After stirring for 2 h, saturated aqueous NaCl (32 mL) was added and about half of THF removed on a rotary evaporator. The remaining solvent was extracted with ether (3×150 mL) and the dried ($Na_2SO_4$) ether layer concentrated to dryness. The residue was purified by flash chromatography (eluent: 10% EtOAc/hexanes) to afford 7.85 g (83%) of 3 as a colorless oil: $R_f$ 0.56 (10% EtOAc/bexanes); $^1H$-NMR (75:15:10 mixture of 2-en-3-ol, 2-α, and 2-β-carbomethoxy-3-keto tautomers) δ11.87 (s, 1H); 3.73 (s, 3H), 3.70 (s, 0.6H), 3.69 (s, 0.4H), 3.42 (m, 0.2H), 3.19 (m, 0.13H), 2.93 (m, 1H), 2.81 (m, 0.13H), 2.71 (m, 0.2H), 2.65 (ddd, 0.13H, J=18, 4, 2 Hz), 2.55 (ddd, 1.2H, J=18, 4, 2 Hz), 2.41 (m, 1H), 2.34 (m, 0.2H), 2.29 (m, 0.13H), 2.03 (dd, 1H, J=18, 2 Hz), 1.65–1.95 (m, 4.4H), 1.30–1.55 (m, 3.6H). $^{13}C$-NMR (only the signals corresponding to the 2-en-3-ol tautomer are reported) δ172.00, 171.19, 105.38, 51.33, 40.19, 35.92, 35.58, 32.91 (2C), 29.90.

2-Carbomethoxy-3-{((trifluoromethyl)sulfonyl)oxy}-bicyclo(3.2.1)-2-octene (4)

To 2-carbomethoxy-bicyclo(3.2.1)octan-3-one, 3 (6.0 g, 3.29 mmol) in THF (120 mL), sodium bis(trimethylsilyl) amide (1.0M solution in THF, 49.4 mL) was added dropwise at −78° C. After stirring for 30 min, N-phenyltrifluoromethane sulfonimide (17.6 g, 4.94 mmol) was added in one portion. After 10 min, the cooling bath was removed and the reaction mixture stirred overnight. Water (100 mL) was added to the reaction mixture and extracted with diethyl ether (3×150 mL). The dried ($Na_2SO_4$) ether layers were concentrated to dryness on a rotary evaporator. The residue was purified by flash chromatography (eluent: 20% EtOAc/hexanes) to afford 7.8 g (75%) of 4 as a colorless oil: $R_f$ 0.56 (20% EtOAc/hexanes); $^1H$-NMR δ3.79 (s, 3H), 3.10 (m, 1H),2.71 (dd, 1H, J=18, 5 Hz), 2.52 (m, 1H), 2.17 (dd, 1H,J=18, 2 Hz), 1.75–2.05 (m, 3H), 1.45–1.70 (m, 3H). $^{13}C$-NMR δ164.44, 151.02, 129.04, 118.23 (q, J=320 Hz), 52.05, 39.68 (d, J=1 Hz), 36.61, 35.34, 34.51, 33.31, 30.01.

2-Carbomethoxy-3-(3,4-dichlorophenyl)-bicyclo(3.2.1)-2-octene (5a)

2-Carbomethoxy-3-{((trifluoromethyl)sulfonyl)oxy}-bicyclo(3.2.1)-2-octene, 4 (2.0 g, 63.6 mmol), 3,4-dichlorophenyl boronic acid (1.58 g, 82.7 mmol), tris (dibenzylideneacetone)dipalladium(0) (0.29 g, 0.32 mmol), $Na_2CO_3$ (2M solution, 6.4 mL) and diethoxymethane (32 mL) were combined and refluxed at 95° C. for 4 h. Tris (dibenzylideneacetone) dipalladium(0) (1.45 g) was then added in five equal portions at 4 h interval. The reaction mixture was cooled to room temperature, filtered through Celite, and washed with ether (200 mL). The ether solution was then washed with saturated aqueous NaCl (100 mL). The dried ($Na_2SO_4$) ether layer was removed on a rotary evaporator. The residue was purified by flash chromatography (eluent: 10% EtOAc/hexanes) to afford 1.38 g (69%) of 5a as a colorless oil: $R_f$ 0.50 (10% EtOAc/hexanes); $^1H$-NMR δ7.34 (d, 1H, J=8 Hz), 7.17 (d, 1H, J=2 Hz), 6.90 (dd, 1H, J 8, 2 Hz) 3.49 (s, 3H), 3.00 (bt, 1H, J=5 Hz), 2.64

(ddd, 1H, J=19, 4, 2 Hz), 2.44 (m, 1H), 2.14 (dd, 1H, J=19, 1 Hz), 1.75–2.05 (m, 3H), 1.45–1.70 (m, 3H). $^{13}$C-NMR δ168.54, 142.60, 142.13, 135.55, 132.07, 130.95, 130.00, 128.80, 126.45, 51.48, 44.52, 37.13, 35.65, 34.86, 33.24, 30.76. Anal. ($C_{16}H_{16}O_2Cl_2$) C, H, Cl.

2-Carbomethoxy-3-naphthyl-bicyclo(3.21)-2-octene (5b)

2-Carbomethoxy-3-{((trifluoromethyl)sulfonyl)oxy}-bicyclo(3.2.1)-2-octene, 4 (0.50 g, 1.60 mmol), 2-naphthaleneboronic acid (0.36 g, 2.08 mmol), tris(dibenzylideneacetone) dipalladium(0) (0.07 g, 0.08 mmol) $Na_2CO_3$ (2M solution, 1.6 mL) and diethoxymethane (8 mL) were combined and refluxed at 95° C. overnight. The reaction mixture was cooled to room temperature, filtered through Celite and washed with ether (100 mL). The ether solution was then extracted with saturated aqueous NaCl (50 mL). The dried ($Na_2SO_4$) ether layer was removed on a rotary evaporator. The residue was purified by flash chromatography (eluent: 10% EtOAc/hexanes) to afford 0.25 g (54%) of 5b as a colorless oil: $R_f$0.41 (10% EtOAc/hexanes); $^1$H-NMR δ7.83 (m, 3H), 7.62 (d, 1H, J=1 Hz), 7.48 (m, 2H), 7.28 (dd, 1H, J=9, 2 Hz), 3.44 (s, 3H), 3.14 (bt, 1H, J=5 Hz), 2.84 (ddd, 1H, J=19, 4, 1 Hz), 2.53 (m, 1H), 2.38 (bd, 1H, J=19 Hz), 1.80–2.20 (m, 4H), 1.60–1.75 (m, 2H). $^{13}$C-NMR δ169.17, 143.83, 139.85, 134.55, 133.04, 132.33, 127.76, 127.47, 127.21, 125.83, 125.54 (2), 124.86, 51.04, 44.35, 37.16, 35.54, 34.82, 33.21, 30.60. Anal. ($C_{20}H_{20}O_2$) C, H.

2-Carbomethoxy-3-(4-fluorophenyl)-bicyclo(3.2.1)-2-octene (5c)

Compound 5c was obtained from with 4-fluorophenylboronic acid as described for 5a: A colorless oil was obtained (73%): $R_f$0.5 (10% EtOAc/hexanes); $^1$H-NMR δ6.95–7.10 (m, 4H), 3.46 (s, 3H), 3.00 (t, 1H, J=5 Hz), 2.67 (dd, 1H, J=19, 4 Hz), 2.46 (m, 1H), 2.20 (bd, 1H, J=19 Hz), 1.50–2.05 (m, 6H). $^{13}$C-NMR δ169.10, 161.86 (d, J=245 Hz), 143.05, 138.32, 134.69, 128.30 (d, J=8 Hz), 114.81 (d, J=21 Hz), 51.18, 44.53, 37.15, 35.55, 34.86, 33.21, 30.65. Anal. ($C_{16}H_{17}O_2F$) C, H.

2-Carbomethoxy-3-phenyl-bicyclo(3.2.1)-2-octene (5d).

Compound 5d was prepared from with phenylboronic acid as described for 5a: A colorless oil was obtained (75%): $R_f$0.5 (10% EtOAc/hexanes); $^1$H-NMR δ7.27 (m, 3H), 7.08 (m, 2H), 3.43 (s, 3H), 3.00 (bt, 1H, J=5), 2.70 (ddd, 1H, J=19, 4, 1 Hz), 2.46 (m, 1H), 2.23 (bd, 1H, J=19 Hz) 1.80–2.05 (m, 3H), 1.73 (d, 1H, J=11 Hz), 1.50–1.65 (m, 2H). $^{13}$C-NMR δ169.31, 144.03, 142.46, 134.28, 127.88, 126.95, 126.61, 51.11, 44.37, 37.17, 35.60, 34.90, 33.26, 30.66. Anal. ($C_{16}H_{18}O_2$) C, H.

2(α, β)-Carbomethoxy-3(α, β)-(4-fluorophenyl)bicyclo(3.2.1)octane (6c)

Magnesium (47 mg, 1.90 mmol) was added into 2-carbomethoxy-3-(4-fluorophenyl)-bicyclo(3.2.1)-2-octene, 5c (50 mg, 0.19 mmol) in methanol (2 mL). After 1 h, additional magnesium (47 mg, 1.90 mmol) was added and stirred for 4 h. 1N HCl (4 mL) was added dropwise and stirred for 1 h. The reaction mixture was extracted with ether (3×20 mL) dried over $Na_2SO_4$ and the ether layer removed on a rotary evaporator. The residue was purified by flash chromatography (eluent: 10% EtOAc/hexanes) to afford 42 mg (84%) of 6c as a colorless oil: $R_f$0.42 (10% EtOAc/hexanes). Anal. ($C_{16}H_{19}FO_2$) C, H.

2(α, β)-Carbomethoxy-3(α, β)-phenylbicyclo(3.2.1)octane (6d)

Compound 6d was prepared from 5d with magnesium as described for 6c. A colorless oil was obtained (48%): $R_f$0.42 (10% EtOAc/hexanes); Anal. ($C_{16}H_{20}O_2$) C, H.

2β-Carbomethoxy-3β-(3,4-dichlorophenyl)-bicyclo(3.2.1) octane (7a)

2α-Carbomethoxy-3β-(3,4-dichlorophenyl)-bicyclo(3.2.1) octane (8a)

2β-Carbomethoxy-3α-(3,4-dichlorophenyl)-bicyclo(3.2.1) octane (9a), and

2α-Carbomethoxy-3α-(3,4-dichlorophenyl)-bicyclo(3.2.1) octane (10a)

To 2-carbomethoxy-3-(3,4-dichlorophenyl)-bicyclo (3.2.1)-2-octene, 5a (1.38 g, 4.43 mmol) in methanol (50 mL) at −78° C., $SmI_2$ (0.1M in THF, 237 mL) was added dropwise via an addition funnel. After completing the addition, the green mixture was stirred for 4 h at −78° C. and quenched with TFA (20 mL) in ether (60 mL). $H_2O$ (50 mL) was added and extracted with ether (3×200 mL). The dried ($Na_2SO_4$) ether layer was concentrated to dryness. The residue was purified by flash chromatography (eluent: 20% EtOAc/hexanes) to afford a mixture of isomers 6a (1 g, 72%). The isomers were separated by gravity column chromatography (eluent: 10–50% toluene/hexanes) to afford 65 mg of 7a as a white solid (mp 81.1–81.4° C.), 280 mg of 8a as a white solid (mp 65.3–65.6° C.), 58 mg of 9a as a white solid (mp 82.8–83.3° C.) and 42 mg of 10a as a white solid (mp 83.2–83.8° C.). 7a: $^1$H-NMR δ7.31 (d, 1H, J=2 Hz), 7.30 (d, 1H, J=8 Hz), 7.08 (ddd, 1H, J=8, 2, 1 Hz), 3.44 (s 3H), 2.98 (ddd, 1H, J=13, 6, 6 Hz), 2.84 (dd, 1H, J=6, 6 Hz), 2.53 (m, 1H), 2.42 (m 1H), 2.31 (ddd, 1H, J=13, 13, 2 Hz), 1.45–2.00 (m, 5H), 1.85 (bd, 1H, J=12 Hz 1.28 (ddd, 1H, J=12, 6, 6 Hz). $^{13}$C-NMR δ173.24, 144.03, 131.86, 129.77, 129.75, 129.63, 126.95, 52.15, 51.05, 38.37, 35.91, 34.54, 33.24, 32.95, 29.59, 28.03. Anal. ($C_{16}H_{18}Cl_2O_2$) C, H, Cl. 8a: $^1$H-NMR δ7.31 (d, 1H, J=8 Hz), 7.30 (d, 1H, J=2 Hz), 7.06 (dd, 1H, J=8, 2 Hz), 3.51 (s, 3H), 3.10 (ddd, 1H, J=12, 12, 6 Hz), 2.66 (dd, 1H, J=12, 2 Hz), 2.48 (m, 1H), 2.32 (m, 1H), 1.87 (m, 1H), 1.45–1.80 (m, 7H). $^{13}$ C-NMR δ173.94, 144.94, 132.11, 130.18, 129.95, 129.61, 127.18, 52.82, 51.40, 40.83, 39.26, 38.70, 38.28, 34.95, 28.60, 25.14. Anal. ($C_{16}H_{18}Cl_2O_2$) C, H, Cl. 9a: $^1$H-NMR 7.30 (d, 1H, J=8 Hz), 7.25 (d, 1H, J=2 Hz) 7.01 (dd, 1H, J=8, 2 Hz), 3.54 (s, 3H), 3.03 (ddd, 1H, J=12, 12, 8 Hz), 2.36 (d, 1H, J=12 Hz), 2.30–2.40 (m, 2H), 2.24 (ddd, 1H, J=12, 8, 8 Hz), 1.94 (m, 1H), 1.92 (bd, 1H, J=12 Hz), 1.74 (m, 1H), 1.56 (m, 1H), 1.44 (m, 1H), 1.20 (dd, 1H, J=12, 12 Hz), 1.10 (ddd, 1H, J=12, 4, 4 Hz). $^{13}$C-NMR δ175.68, 145.19, 132.14, 130.18, 130.05, 129.70, 127.30, 55.93, 51.60, 38.92, 36.99, 36.70, 33.44, 32.89, 31.76, 29.83. Anal. ($C_{16}H_{18}Cl_2O_2$) C, H, Cl. 10a: $^1$H-NMR δ7.31 (dd, 1H, J=2, 1 Hz), 7.28 (d, 1H, J=8 Hz), 7.07 (ddd, 1H, J=8, 2, 1 Hz), 3.45 (s, 3H), 3.31 (dd, 1H, J=6, 6 Hz), 3.11 (ddd, 1H, J=12, 6, 6 Hz), 2.64 (m, 1H), 2.37 (m, 1H), 2.16 (ddd, 1H, J=12, 6, 6 Hz), 1.95 (bdd, 1H, J=12, 12 Hz), 1.82 (bd, 1H, J=12 Hz), 1.73 (m, 1H), 1.50–1.65 (m, 2H), 1.42 (m, 1H), 1.28 (ddd, 1H, J=12, 4, 4 Hz). $^{13}$C-NMR δ173.70, 144.18, 131.76, 129.88, 129.61, 129.48, 127.04, 50.89, 50.11, 35.23, 34.49, 34.47, 33.54, 32.31, 32.02, 27.02. Anal. ($C_{16}H_{18}Cl_2O_2$) C, H, Cl.

2β-Carbomethoxy-3β-naphthyl-bicyclo(3.2.1)octane (7b)

2α-Carbomethoxy-3β-naphthyl-bicyclo(3.2.1)octane (8b)

2β-Carbomethoxy-3α-naphthyl-bicyclo(3.21)octane (9b) and

2α-Carbomethoxy-3α-naphthyl-bicyclo(3.2.1)octane (10b)

To 2-carbomethoxy-3-naphthyl-bicyclo (3.2.1)-2-octene, 5b (0.75 g, 2.57 mmol) in methanol (30 mL) at −78° C., $SmI_2$ (0.1 M in THF, 200 mL) was added dropwise via an addition funnel. After completing the addition, the green mixture was stirred for 4 h at −78° C. and quenched with TFA (10 mL) in ether (30 mL). $H_2O$ (25 mL) was added and extracted with ether (3×100 mL). The dried ($Na_2SO_4$) ether layer was concentrated to dryness. The residue was purified by flash chromatography (eluent: 10% EtOAc/hexanes) to afford a mixture of isomers, 6b (0.48 g, 64%). The isomers were separated by gravity column chromatography (eluent: 40–80% toluene/hexanes) to afford 20 mg of 7b as a white solid (mp 78.8–79.1° C.), 30 mg of 8b as a white solid (mp 71.3–71.7° C.), 50 mg of 9b as a white solid (mp 71.1–71.4° C.), and 10b as a white solid (mp 91.1–91.3° C.). 7b: $^1$H-NMR δ7.77 (m, 2H), 7.73 (d, 1H, J=9 Hz), 7.68 (bs, 1H), 7.41 (m, 3H), 3.32 (s, 3H), 3.22 (ddd, 1H, J=12, 6, 6 Hz), 3.00 (dd, 1H, J=6, 4 Hz), 2.56 (m, 1H), 2.54 (m, 1H), 2.48 (m, 1H), 2.00 (bd, 1H, J=12 Hz), 1.92 (m, 1H), 1.55–1.85 (m, 4H), 1.32 (ddd, 1H, J=12, 6, 6 Hz). $^{13}$C-NMR δ173.76, 141.10, 133.49, 132.16, 127.90, 127.52, 127.42, 126.45, 125.98, 125.75, 125.26, 52.55, 50.96, 38.60, 36.83, 34.85, 33.58, 33.16, 29.92, 28.29. Anal. ($C_{20}H_{22}O_2$) C, H. 8b: $^1$H-NMR δ7.76(m, 3H), 7.66 (bd, 1H, J=2 Hz), 7.40 (m, 3H), 3.43 (s, 3H), 3.31 (ddd, 1H, J=12, 12, 6 Hz), 2.88 (dd, 1H, J=12, 2 Hz), 2.51 (m, 1H), 2.35(m, 1H), 2.00 (m, 1H), 1.50–1.85 (m, 7H). $^{13}$C-NMR δ174.56, 142.13, 133.66, 132.41, 127.99, 127.77, 127.61, 126.44, 126.12, 125.85, 125.32, 53.14, 51.41, 41.27, 39.60, 39.18, 39.00, 35.33, 28.93, 25.39. Anal. ($C_{20}H_{22}O_2$) C, H. 9b: $^1$H-NMR δ7.77(m, 3H), 7.63 (bs, 1H), 7.44 (m, 2H), 7.34 (dd, 1H, J=9, 2 Hz), 3.48 (s, 3H), 3.26 (ddd, 1H, J=11, 11, 7 Hz), 2.58 (d, 1H, J=11 Hz) 2.35–2.45 (m, 2H), 2.32 (ddd, 1H, J=12, 7, 7 Hz), 2.05 (bd, 1H, J=12 Hz), 1.96 (m, 1H), 1.78 (m, 1H), 1.66 (m, 1H), 1.52 (m, 1H), 1.40 (dd, 1H, J 12, 12 Hz), 1.15 (ddd, 1H, J=12, 4, 4 Hz). $^{13}$C-NMR δ176.34, 142.24, 133.55, 132.32, 128.03, 127.71, 127.61, 126.35, 126.26, 125.90, 125.35, 56.10, 51.58, 39.24, 37.59, 37.25, 33.65, 33.08, 32.07, 30.09. Anal. ($C_{20}H_{22}O_2$) C, H.

2α-Carbomethoxy-3α-naphthyl-bicyclo(3.2.1)octane (10b)

Compound 5b (200 mg, 0.68 mmol) was hydrogenated under pressure (50 psi) in the presence of Pd-C (10% w/w 118 mg) in methanol (40 mL) overnight. The resulting mixture was filtered through Celite and the methanol evaporated. The crude residue (180 mg) contained a mixture of products and was purified by gravity column chromatography on flash silica (eluent: 40–8-% toluene/hexanes) to afford 85 mg of a white solid. Recrystallization from ethanol gave analytically pure 10b (70 mg), mp 91.1–91.3° C.; $^1$H-NMR δ7.75 (m, 3H), 7.70 (bs, 1H), 7.40 (m, 3H), 3.35–3.45 (m, 2H), 3.36 (s, 3H), 2.70 (m, 1H), 2.40 (m, 1H), 2.29 (ddd, 1H, J=12, 7, 7 Hz), 2.20 (ddd, 1H, J=12, 12, 2 Hz), 1.89 (bd, 1H,J=12 Hz), 1.50–180 (m, 3H), 1.45 (m, 1H), 1.35 (ddd, 1H, J=12, 4, 4 Hz). $^{13}$C-NMR δ174.35, 141.37, 133.36, 131.88, 127.90, 127.45, 127.29, 126.87, 125.75, 125.72, 125.24, 52.55, 50.96, 38.60, 36.83, 34.85, 33.58, 33.16, 29.92, 28.29. Anal. ($C_{20}H_{22}O_2$) C, H.

B. Synthesis of 3-ary-8-oxabicyclo (3.2.1)octanes

Schemes 2 and 3 (FIGS. 3 and 4) show the synthesis of 3-ary-8-oxabicyclo (3.2.1)octanes.

(1R,1S)-2-Carbomethoxy-3-{((trifluoromethyl)sulfonyl)oxy)-}8-oxabicyclo(3.2.1)-2-octene (14)

Sodium bis(trimethylsilyl)amide (1.0 M solution in THF, 45 mL) was added dropwise to 2-carbomethoxy-8-oxabicyclo(3.2.1) octanone, 13$^{25}$ (7.12 g, 38.65 mmol) in THF (100 mL) at −70° C. under nitrogen. After stirring for 30 min, N-phenyltrifluoromethanesulfonimide (15.19 g, 42.52 mmol) was added as a solid at −70° C. The reaction was allowed to warm to room temperature and was then stirred overnight. The volatiles were removed on a rotary evaporator. The residue was dissolved in $CH_2Cl_2$ (200 mL) and washed with $H_2O$ (100 mL) and brine (100 mL). The dried ($MgSO_4$) $CH_2Cl_2$ layer was concentrated to dryness on a rotary evaporator. The residue was purified by flash chromatography (eluent: 5%–10% EtOAc/hexanes) to afford 9.62 g (79%) of 14 as a pale yellow oil: $^1$H-NMR (CDCl$_3$, 100 MHz): δ5.0–5.1 (m, 1H), 4.6–4.8 (m, 1H), 3.83 (s, 3H), 3.0 (dd, 1H, J=5, 8 Hz), 1.7–2.35 (m, 5H).

General Procedure for Synthesis of the 2-Octenes: (1R,1S)-2-Carbomethoxy-3-phenyl-8-oxabicyclo(3.2.1)-2-octene (15a)

2-Carbomethoxy-3-{((trifluoromethyl)sulfonyl)oxy}-8-oxabicyclo(3.2.1)-2-octene, 14 (2.0 g, 6.32 mmol), phenyl boronic acid (1.02 g, 8.36 mmol), diethoxymethane (20 mL), LiCl (578 mg, 13.6 mmol), tris(dibenzylideneacetone) dipalladium(0) (247 mg, 0.25 mmol) and $Na_2CO_3$ (2 M solution, 6.1 mL) were combined and heated at reflux for 1 h. The mixture was cooled to room temperature, filtered through Celite and washed with ether (100 mL). The mixture was basified with $NH_4OH$ and washed with brine. The dried ($MgSO_4$) ether layer was concentrated to dryness. The residue was purified by flash chromatography (eluent: 10% EtOAc/hexanes) to afford 1.28 g (82%) of 15a as a light brown viscous oil: R$_f$0.26 (20% EtOAc/hexanes); $^1$H-NMR (CDCl$_3$, 100 MHz): δ7.1–7.5 (m, 5H), 4.95–5.1 (m, 1H), 4.55–4.75 (m, 1H), 3.52 (s, 3H), 2.95 (dd, 1H, J=5, 18 Hz), 1.7–2.2 (m, 5H). Anal. ($C_{15}H_{16}O_3$) C, H.

(1R,1S)-2-Carbomethoxy-3-(4-fluorophenyl)-8-oxabicyclo (3.2.1)-2-octene (15b)

Compound 15b was prepared from 14 with 4-fluorophenylboronic acid as described for 15a. A light brown viscous oil was obtained (88%): R$_f$0.19 (20% EtOAc/hexanes); $^1$H-NMR (CDCl$_3$, 100 MHz): δ7.0–7.2 (m, 4H), 4.95–5.05 (m, 1H), 4.55–4.75 (m, 1H), 3.52 (s, 3H), 2.95 (dd, 1H, J=5, 18 Hz), 1.7–2.3 (m, 5H). Anal. ($C_{15}H_{15}O_3F$) C, H.

(1R,1S)-2-Carbomethoxy-3-(4-chlorophenyl)-8-oxabicyclo (3.2.1)-2-octene (15c)

Compound 15c was prepared from 14 with 4-chlorophenylboronic acid as described for 15a. A light brown viscous oil was obtained (92%): R$_f$0.23 (20% EtOAc/hexanes); $^1$H-NMR (CDCl$_3$, 100 MHz): δ7.0–7.4 (m, 4H), 4.95–5.1 (m, 1H), 4.55–4.75 (m, 1H), 3.52 (s, 3H), 2.95 (dd, 1H, J=5, 18 Hz), 1.7–2.2 (m, 5H). Anal. ($C_{15}H_{15}O_3Cl$) C, H, Cl.

(1R,1S)-2-Carbomethoxy-3-(4-bromophenyl)-8-oxabicyclo (3.2.1)-2-octene (15d)

Compound 15d was prepared from 14 with 4-bromophenylboronic acid as described for 15a. A clear viscous oil was obtained (41%): R$_f$0.39 (20% EtOAc/hexanes); $^1$H-NMR (CDCl$_3$, 100 MHz): δ7.48 (d, 2H, J=9 Hz), 6.97 (d, 2H, 9 Hz), 4.95–5.1 (m, 1H), 4.5–4.75 (m, 1H), 3.52 (s, 3H), 2.95 (dd, 1H, J=5, 18 Hz), 1.65–2.4 (m, 5H). Anal. ($C_{15}H_{15}O_3Br$) C, H, Br.

(1R,1S)-2-Carbomethoxy-3-(3,4-dichlorophenyl)-8-oxabicyclo(3.2.1)-2-octene (15f)

Compound 15f was prepared from 14 with 3,4-chlorophenylboronic acid as described for 15a. A light brown viscous oil was obtained (97%): R$_f$0.45 (30% EtOAc/hexanes); $^1$H-NMR (CDCl$_3$, 100 MHz): δ7.4 (d, 1H, J=10 Hz), 7.23 (d, 1H, J=2 Hz), 6.95 (dd, 1H, J=2, 10 Hz), 4.95–5.1 (m, 1H), 4.55–4.75 (m, 1H), 3.52 (s, 3H), 2.95 (dd, 1H, J=5, 18 Hz), 1.6–2.3 (m, 5H). Anal. ($C_{15}H_{14}O_3Cl_2$) C, H, Cl (1R)-2-Carbomethoxy-3-(3,4-dichlorophenyl)-8-oxabicyclo (3.2.1)-2-octene (15g)

Compound 15g was prepared from (1R)-14 with 3,4-chlorophenylboronic acid as described for 15a. A light brown viscous oil was obtained (94%): R$_f$0.45 (30% EtOAc/hexanes); $^1$H-NMR (CDCl$_3$, 100 MHz): identical to 5f above.

(1S)-2-Carbomethoxy-3-(3,4-dichlorophenyl)-8-oxabicyclo (3.2.1)-2-octene (15h)

Compound 15h was prepared from (1S)-14 with 3,4-chlorophenylboronic acid as described for 15a. A clear viscous oil was obtained (80%): $R_f$ 0.45 (30% EtOAc/iexanes); $^1$H-NMR (CDCl$_3$, 100 MHz): identical to 15f above.

General Procedure for Synthesis of the Octanes: (1R,1S)-2β-Carbomethoxy-3β-phenyl-8-oxabicyclo(3.2.1)octane (16a) and (1R,1S)-2β-Carbomethoxy-3α-phenyl-8-oxabicyclo(3.2.1)octane (17a)

To 2-carbomethoxy-3-phenyl-8-oxabicyclo(3.2.1)-2-octene, 15a (1.17 g, 4.8 mmol) in THF (10 mL) at −70° C. under N$_2$ was added SmI$_2$ (0.1 M in THF, 215 mL, 21.5 mmol). After the mixture was stirred for 30 min, MeOH (anhydrous, 25 mL) was added. The mixture was stirred at −70° C. for a further 2 h. The mixture was quenched with TFA (5 mL) and H$_2$O (100 mL). After warming to 0° C., NH$_4$OH was added to attain pH 11 and the mixture was then stirred for 30 min. The mixture was filtered through Celite and washed with ether (400 mL) and then saturated with Na$_2$S$_2$O$_3$. The ether layer was washed with brine. The dried (MgSO$_4$) ether layer was concentrated to dryness. The isomers were separated by gravity column chromatography (eluent: 10% EtOAc/hexanes) to afford 270 mg (23%) of 16a as a white solid: mp 102.5–104° C.; $R_f$ 0.30 (30% EtOAc/hexanes); and 789 mg (67%) of 17a as a white solid: mp 96.5–98° C.; $R_f$ 0.37 (30% EtOAc/hexanes); (16a): $^1$H-NMR (CDCl$_3$, 100 MHz): δ7.25 (br s, 5H), 4.55–4.8 (m, 2H), 3.48 (s, 3H), 3.25 (ddd, 1H, J=5, 5, 14 Hz), 2.6–3.0 (m, 2H), 1.5–2.3 (m, 5H). Anal. (C$_{15}$H$_{18}$O$_3$) C, H. (17a): $^1$H-NMR (CDCl$_3$, 100 MHz): δ7.25 (br s, 5H), 4.4–4.65 (m, 2H), 3.58 (s, 3H), 3.25 (ddd, 1H, J=7, 11, 11 Hz), 2.52 (dd, 1H, J=2, 11 Hz), 1.6–2.5 (m, 5H), 1.41 (ddd, 1H, J=2, 11, 14 Hz). Anal. (C$_{15}$H$_{18}$O$_3$) C, H.

(1R,1S)-2β-Carbometboxy-3β-(4-fluorophenyl)-8-oxabicyclo(3.2.1)octane (16b) and (1R,1S)-2β-Carbomethoxy-3α-(4-fluorophenyl)-8-oxabicyclo (3.2.1) octane (17b)

Compounds 16b and 17b were prepared from 15b as described for compounds 16a and 17a. Compound 16b was obtained (22%) as a white solid: mp 118–120.5° C.; $R_f$ 0.27 (30% EtOAc/hexanes); and 17b (62%) as a white solid: mp 58–60° C.; $R_f$ 0.36 (30% EtOAc/hexanes). (16b): $^1$H-NMR (CDCl$_3$, 400 MHz): δ7.15–7.25 (m, 2H), 6.9–7.0 (m, 2H), 4.6–4.7 (m, 2H), 3.48 (s, 3H), 3.17 (ddd, 1H, J=5, 5, 13 Hz), 2.78 (d, 1H, J=5 Hz), 2.73 (ddd, 1H, J =4, 13, 13 Hz), 1.7–2.2 (m, 4H), 1.5–1.65 (m, 1H). Anal. (C$_{15}$H$_{17}$O$_3$F) C, H. (17b): $^1$H-NMR (CDCl$_3$, 400 MHz): δ7.1–7.2 (m, 2H), 6.9–7.0 (m, 2 h), 4.5–4.8 (m, 2H), 3.55 (s, 3H), 3.20 (ddd, 1H, J=7, 11, 11 Hz), 2.44 (dd, 1H, J=2, 11 Hz), 2.38 (ddd, 1H, J=7, 9, 13 Hz), 1.9–2.2 (m, 2H), 1.76 (ddd, 1H, J=5, 9, 13 Hz), 1.6–1.7 (m, 1H), 1.32 (ddd, 1H, J=2, 11, 13 Hz). Anal. (C$_{15}$H$_{17}$O$_3$F) C, H.

(1R,1S)-2β-Carbomethoxy-3β-(4-chlorophenyl)-8-oxabicyclo(3.2.1)octane (16c) and (1R,1S)-2β-Carbomethoxy-3α-(4-chlorophenyl)-8-oxabicyclo (3.2.1) octane (17c)

Compounds 16c and 17c were prepared from 15c as described for compounds 16a and 17a. Compound 16c was obtained (19%) as a white solid: mp 116–117° C.; $R_f$ 0.27 (30% EtOAc/hexanes); and 17c (51%) as a white solid: mp 89–90° C.; $R_f$ 0.32 (30% EtOAc/hexanes). (16c): $^1$H-NMR (CDCl$_3$, 100 MHz): δ7.1–7.4 (m, 4H), 4.55–4.8 (m, 2H), 3.55 (s, 3H), 3.20 (ddd, 1H, J=5, 5, 12 Hz), 2.55–2.95 (m, 2H), 1.5 –2.3 (m, 5H). Anal. (C$_{15}$H$_{17}$O$_3$Cl) C, H, Cl. (17c): $^1$H-NMR (CDCl$_3$, 100 MHz): δ7.1–7.4 (m, 4H), 4.4–4.65 (m, 2H), 3.58 (s, 3H), 3.05–3.45 (m, 1H), 1.2–2.6 (m, 7H). Anal. (C$_{15}$H$_{17}$O$_3$Cl) C, H, Cl.

(1R,1S)-2β-Carbomethoxy-3α-(4-bromophenyl)-8-oxabicyclo(3.2.1)octane (16d) and (1R,1S)-2β-Carbomethoxy-3β-(4-bromophenyl)-8-oxabicyclo(3.2.1)octane (17d)

Compounds 16d and 17d were prepared from 15d as described for compounds 16a and 17a except no TFA was used when quenching. Compound 16d was obtained (47%) as a white solid: mp 113–115° C.; $R_f$ 0.29 (30% EtOAc/hexanes); and 17d (32%) as a white solid: mp 96–98° C.; $R_f$ 0.38 (30% EtOAc/hexanes). (16d): $^1$H-NMR (CDCl$_3$, 100 MHz): δ7.45 (d, 2H, J=9 Hz), 7.15 (d, 2H, J=9 Hz), 4.6–4.8 (m, 2H), 3.5 (s, 3H), 3.0–3.4 (m, 1H), 2.55–2.9 (m, 2H), 1.5–2.4 (m, 5H). Anal. C$_{15}$H$_{17}$O$_3$Br. (17d): $^1$H-NMR (CDCl$_3$, 100 MHz): δ7.45 (d, 2H, J=10 Hz), 7.1 (d, 2H, J=10 Hz), 4.4–4.6 (m, 2H), 3.53 (s, 3H), 3.20 (ddd, 1H, J=6, 11, 11 Hz), 1.6–2.6 (m, 6H), 1.35 (ddd, 1H, J=2, 11, 13 Hz). Anal. (C$_{15}$H$_{17}$O$_3$Br) C, H, Br.

(1R,1S)-2β-Carbomethoxy-3β-(3,4-dichlorophenyl)-8-oxabicyclo(3.2.1) octane (16f) and (1R,1S)-2β-Carbomethoxy-3β-(3,4-dichlorophenyl)-8-oxabicyclo (3.2.1)octane (17f).

Compounds 16f and 17f were prepared from 15f as described for compounds 16a and 7a. Compound 16f was obtained (14%) as a white solid: mp. 132–133.5° C.; $R_f$ 0.31 (30% EtOAc/hexanes); and 17f (55%) as a white solid: mp. 88.5–90° C.; $R_f$ 0.33 (30% EtOAc/hexanes). (6f): $^1$H-NMR (CDCl$_3$, 100 MHz): δ7.0–7.5 (m, 3H), 4.55–4.85 (m, 2H), 3.55 (s, 3H), 3.20 (ddd, 1H, J=5, 5, 11 Hz), 2.55–2.95 (m, 2H), 1.45–2.35 (m, 5H). Anal. (C$_{15}$H$_{16}$O$_3$Cl$_2$) C, H, Cl. (17f): $^1$H-NMR (CDCl$_3$, 100 MHz): δ7.0–7.5 (m, 3H), 4.4–4.65 (m, 2H), 3.60 (s, 3H), 3.20 (ddd, 1H, J=7, 11, 11 Hz), 1.5–2.5 (m, 6H), 1.30 (ddd, 1H, J=2, 11, 13 Hz). Anal. (C$_{15}$H$_{16}$O$_3$Cl$_2$) C, H, Cl.

(1R)-2β-Carbomethoxy-3β-(3,4-dichlorophenyl)-8-oxabicyclo(3.2.1) octane (16g) and (1R)-2β-Carbomethoxy-3α-(3,4-dichlorophenyl)-8-oxabicyclo(3.2.1)octane (17g)

Compounds 16g and 17g were prepared from (1R)-15f as described for compounds 16a and 17a. Compound 16g was obtained (13%) as a white solid: mp 121–122° C.; $R_f$ 0.31 (30% EtOAc/hexanes); and 17g (45%) as a white solid: mp 103.5–104.5° C.; $(\alpha)^{21}_D$=−79° (c=1, MeOH); $R_f$ 0.33 (30% EtOAc/hexanes). (16g and 17g): $^1$H-NMR (CDCl$_3$, 100 MHz): identical to 16f and 17f above. Anal. (C$_{15}$H$_{16}$O$_3$Cl$_2$) C, H, Cl.

(1S)-2β-Carbomethoxy-3β-(3,4-dichlorophenyl)-8-oxabicyclo(3.2.1) octane (16h) and (1S)-2β-Carbometboxy-3α-(3,4-dichlorophenyl)-8-oxabicyclo(3.2.1)octane (17h). C Compounds 16h and 17h were prepared from (1S)-15f as described for compounds 16a and 17a. Compound 16h was obtained (11%) as a white solid: mp 121–122° C.; $R_f$ 0.31 (30% EtOAc/hexanes); and 17h (45%) as a white solid: mp 103–104° C.; $(\alpha)^{21}_D$=+76° (c=1, MeOH); $R_f$ 0.33 (30% EtOAc/hexanes). (16h and 17h): $^1$H-NMR (CDCl$_3$, 100 MHz): identical to 16f and 17f above. Anal. (C$_{15}$H$_{16}$O$_3$Cl$_2$) C, H, Cl.

Synthesis of (1R,1S)-2-Carbomethoxy-3-(4-iodophenyl)-8-oxabicyclo(3.2.1)-2-octene, 15e: (1R,1S)-2-Carbomethoxy-3-(4-tributylstannylphenyl)-8-oxabicyclo(3.2.1.)-2-octene 2-Carbomethoxy-3-(4-bromophenyl)-8-oxabicyclol{3.2.1)-2-octene, 15d (200 mg, 0.62 mmol), tetrakis (triphenylphosphine)palladium(0) (13 mg, 0.011 mmol) and bis(tributyltin) (0.74 mL, 1.46 mmol) in toluene (4 mL) were degassed by bubbling N$_2$ through the solution for 10 min.

The mixture was then heated at reflux for 6 h. CH$_2$Cl$_2$ (10 mL) was added and the mixture was filtered through Celite. The filtrate was concentrated to dryness. The residue was purified sequentially by flash chromatography (eluent: 30% EtOAc/hexanes) and preparative TLC (eluent: 5%–10% EtOAc/hexanes) to afford 206 mg (62%) of the title compound as a clear viscous oil: R$_f$0.31 (59% EtOAc/hexanes); $^1$H-NMR (CDCl$_3$, 100 MHz): δ7.43 (d, 2H, J=7 Hz), 7.05 (d, 2H, J=7 Hz), 4.95–5.1 (m, 1H), 4.55–4.75 (m, 1H), 3.50 (s, 3H), 2.95 (dd 1H, J=5, 18 Hz), 0.7–2.3 (m, 32H).

(1R,1S)-2-Carbomethoxy-3-(4-iodophenyl)-8-oxabicyclo (3.2.1)-2-octene (15e)

2-Carbomethoxy-3-(4-tributylstannylphenyl)-8-oxabicyclo(3.2.1)-2-octene (206 mg, 0.39 mmol) from above, in THF (anhydrous, 5 mL) was degassed by bubbling N$_2$ for 10 min. N-Iodosuccinimide (96 mg, 0.43 mmol) was added. The reaction mixture was stirred at room temperature for 1 h and concentrated to dryness. The residue was dissolved in ether (10 mL), washed with saturated NaHCO$_3$ and brine. The dried (MgSO$_4$) ether layer was concentrated to dryness. The residue was purified by flash chromatography (eluent: 10% EtOAc/hexanes) and preparative TLC (eluent: 30% EtOAc/hexanes) to afford 128 mg (90%) of 15e as a pale yellow viscous oil: R$_f$0.49 (30% EtOAc/hexanes); $^1$H-NMR (CDCl$_3$, 100 MHz): δ7.68 (d, 2H, J=10 Hz), 6.85 (d, 2H, J=10 Hz), 4.95–5.05 (m, 1H), 4.55–4.75 (m, 1H), 3.54 (s, 3H), 2.95 (dd, 1H, J=5, 18 Hz), 1.55–2.40 (m, 5H). Anal. (C$_{15}$H$_{15}$O$_3$I) C, H, I.

Synthesis of (1R,1S)-2β-Carbomethoxy-3α-(4-iodophenyl)-8-oxabicyclo(3.2.1)octane (17e): (1R,1S)-2β-Carbomethoxy-3α-(4-tributylstannylphenyl)-8-oxabicyclo (3.2.1) octane The title compound was prepared from 17d, as described above for stannylation of 15d. A clear viscous oil (41%) was obtained: R$_f$0.48 (30% EtOAc/hexanes); $^1$H-NMR (CDCl$_3$, 100 MHz): δ7.4 (d, 2H, J=7 Hz), 7.2 (d, 2H, J=7 Hz), 4.4–4.6 (m, 2H), 3.60 (s, 3H), 3.25 (ddd, 1H, J=6, 10, 10 Hz), 0.7–2.65 (m, 34H).

(1R,1S)-2β-Carbomethoxy-3α-(4-iodophenyl)-8-oxabicyclo(3.2.1)octane (17e).

Compound 17e was prepared from the above stannyl compound as described for 15e from 2β-carbomethoxy-3α-(4-tributylstannylphenyl)-8-oxabicyclo(3.2.1) octane (85%). A white solid was obtained: mp 124–126° C.; R$_f$0.36 (30% EtOAc/hexanes); $^1$H-NMR (CDCl$_3$, 100 MHz): δ7.6 (d, 2H, J=9 Hz), 6.97 (d, 2H, J=9 Hz), 4.35–4.65 (m, 2H), 3.6 (s, 3H), 3.2 (ddd, 1H, J=6, 11, 11 Hz), 1.5–2.6 (m 6H), 1.35 (ddd, 1H, J=2, 11, 13 Hz). Anal. (C$_{15}$H$_{17}$O$_3$I) C, H, I.

Synthesis of (1R,1S)-2β-Carbomethoxy-3β-(4-iodophenyl)-8-oxabicyclo(3.2.1)octane (16e): (1R,1S)-2β-Carbomethoxy-3β-(4-nitrophenyl)-8-oxabicyclo(3.2.1)octane To 2β-carbomethoxy-3β-phenyl-8-oxabicyclo(3.2.1) octane, 16a (112 mg, 0.45 mmol) in CH$_3$CN (anhydrous, 5 mL) at −5° C. was added NO$_2$BF$_4$ (83 mg, 0.63 mmol). The reaction mixture was stirred at −5° C. for 3 h. A small amount of ice was added and the mixture was stirred at −25° C. for 15 min. The CH$_3$CN was removed, the melted ice was extracted with ether. The combined ether extract and CH$_3$CN solution were concentrated to dryness. The residue was dissolved in ether (50 mL), washed with saturated NaHCO$_3$ and brine. The dried (MgSO$_4$) ether layer was concentrated to dryness. The residue was purified by flash chromatography (eluent: 10%–20% EtOAc/hexanes) to afford 75.6 mg (57%) of the title 4-nitro-compound: R$_f$0.19 (30% EtOAc/hexanes); $^1$H-NMR (CDCl$_3$, 100 MHz) δ8.2 (d, 2H, J=10 Hz), 7.42 (d, 2H, J=10 Hz), 4.6–4.85 (m, 2H), 3.54 (s, 3H), 3.15–3.45 (m, 1H), 2.6–3.0 (m, 2H), 1.7–2.4 (m, 5H).

(1R,1S)-2β-Carbomethoxy-3β-(4-aminophenyl)-8-oxabicyclo(3.2.1)octane

2β-Carbomethoxy-3β-(4-nitrophenyl)-8-oxabicyclo (3.2.1)octane (75.6 mg, 0.026 mmol) in MeOH (20 mL) was hydrogenated overnight at room temperature using Raney Ni (50%) as catalyst. The reaction mixture was filtered through Celite, washed with MeOH and concentrated to dryness. The residue was purified by flash chromatography (eluent: 20%–30% EtOAc/hexanes) to afford 43 mg (75%) of the title 4-amino-compound: R$_f$0.22 (50% EtOAc/hexanes); $^1$H-NMR (CDCl$_3$, 100 MHz) δ7.05 (d, 2H, J=9 Hz), 6.62 (d, 2H, J=9 Hz), 4.55–4.7 (m, 2H), 3.58 (br s, 2H), 3.50 (s, 3H), 3.0–3.3 (m, 1H), 2.5–2.9 (m, 2H), 1.4–2.3 (m, 5H).

(1R,1S)-2β-Carbomethoxy-3β-(4-iodophenyl)-8-oxabicyclo(3.2.1)octane (16e)

To 2β-carbomethoxy-3β(4-aminophenyl)-8-oxabicyclo (3.2.1)octane (26 mg, 0.099 mmol) in CH$_2$I$_2$ (2 mL) under N$_2$ was added isoamyl nitrite (0.17 mL, 0.126 mmol). The reaction mixture was stirred at room temperature for 1 h then at 55° C. for 3 h. CH$_2$I$_2$ was removed under reduced pressure. The residue was purified by flash chromatography (eluent: 10% EtOAc/hexanes) to afford 15 mg (60%) of 6e as a white solid: mp 119–120.5° C.; R$_f$ 0.25 (30% EtOAc/hexanes); $^1$H-NMR (CDCl$_3$, 100 MHz) δ7.65 (d, 2H, J=9 Hz), 7.00 (d, 2H, J=9 Hz), 4.6–4.8 (m, 2H), 3.52 (s, 3H), 3.05–3.3 (m 1H), 2.55–2.9 (m, 2H), 1.5–2.3 (m, 5H).

(1R,1S)-2-Carbomethoxy-3-(4-acetylphenyl)-8-oxabicyclo(3.2.1)-2-octene (15i)

Compound 15i was prepared from 14 with 4-acetylphenylboronic acid as described for 15a. A light yellow solid was obtained (64%): m.p. 120–121 C; R$_f$0.22 (30% EtOAc/hexanes); $^1$HNMR δ(CDCl$_3$, 300 MHz): 7.93 (d, 2H), 7.20 (d, 2H), 5.02 (d, 1H), 4.66 (t, 1H), 3.52 (s, 3H), 2.96 (dd, 1H), 2.60 (s, 3H), 2.29–2.06 (m, 4H), 1.83–1.73 (m, 1H). Anal. (C$_{17}$H$_{18}$O$_4$) C, H.

(1R,1S)-2-Carbomethoxy-3-(4-isopropylphenyl)-8-oxabicyclo(3.2.1)-2-octene (15j)

Compound 15j was prepared from 14 with 4-isopropylphenylboronic acid as described for 15a. A light yellow oil was obtained (80%): R$_f$0.46 (30% EtOAc/hexanes); $^1$HNMR (CDCl$_3$, 300 MHz): δ7.17 (d, 2H), 7.04 (d, 2H), 4.99 (d, 1H), 4.63 (t, 1H), 3.51 (s, 3H), 3.02–2.85 (m, 2H), 2.26–2.04 (m, 4H), 1.8–1.73 (m. 1H), 1.23 (d, 6H). Anal. (C$_{18}$H$_{22}$O$_3$) C, H.

(1R,1S)-2-Carbomethoxy-3-(4-isopropenylphenyl)-8-oxabicyclo(3.2.1)-2-octene (15k)

Compound 15k was prepared from 15i as follows: Methyltriphenylphosphonium bromide (0.35 g, 1.0 mmol) was dissolved in anhydrous THF (5 mL) under N$_2$ and cooled to −78 C. nButyllithium (0.46 mL, 2.5 M in THF, 1.15 mmol) was added slowly. This mixture was stirred for 20 min at −78 C. (1R, 1S)-2-Carbomethoxy-3-(4-acetylphenyl)-8-oxabicyclo(3.2.1)-2-octene (5i, 0.22 g, 0.77 mmol) in THF (2 mL) cooled at 0 C. was added via canula. The resulting mixture was allowed to warm up to room temperature and was stirred at room temperature for 23 h. The reaction was quenched by water (25 mL). This was extracted with ether (40 mL). The ether extract was washed with brine, dried over sodium sulfate and evaporated to dryness. The residue was purified by flash column chromatography to afford 118 mg white solid (54%): R$_f$0.45 (30% EtOAc/hexanes); $^1$HNMR (CDCl$_3$, 300 MHz): δ7.43 (d, 2H), 7.09 (d, 2H), 5.40 (s, 1H), 5.09 (s, 1H), 5.01 (d, 1H), 4.65 (t, 1H), 3.54 (s, 3H), 2.96 (dd, 1H), 2.26–2.05 (m, 7H), 1.83–1.74 (m, 1H). Anal. (C$_{18}$H$_{20}$O$_3$) C,H.

(1R,1S)-2-Carbomethoxy-3-(4-propynylphenyl)-8-oxabicyclo(3.2.1)-2-octene (15l)

Compound 15l was prepared from 15m and propynyltributyltin as follows: (1R,1S)-2-Carbomethoxy-3-(4-bromophenyl)-8-oxabicyclo(3.2.1)-2-octene (15m, 0.5 g, 1.55 mmol) and propynyltributyltin (0.62 g, 1.88 mmol) were combined in anhydrous toluene (40 mL) and $N_2$ was bubbled through for 10 min. This solution was added via canula to a flask charged with tetrakis(triphenylphosphine)palladium(0) (0.18 g, 0.16 mmol) protected under $N_2$. The resulting solution was heated at reflux for 5 h. The reaction solution was cooled to room temperature and diluted with ether (50 mL). This was filtered through celite. The filtrate was evaporated to dryness. The residue was purified by flash column chromatography to afford 181 mg off-white solid (42%). Recrystalization of this slightly impure product (99 mg) from EtOAc/hexanes afforded a pure product (while solid, 62 mg): m.p. 93.5–94 C; $R_f$ 0.40 (30% EtOAc/hexanes); $^1$HNMR (CDCl$_3$, 300 MHz): δ7.33 (d, 2H), 7.02 (d, 2H), 4.99 (d, 1H), 4.63 (t, 1H), 3.48 (s, 3H), 2.96 (dd, 1H), 2.25–2.06 (m, 4H), 2.04 (s, 3H), 1.82–1.71 (m, 1H). Anal. ($C_{18}H_{18}O_3$) C, H.

(1R,1S)-2β-Carbomethoxy-3β-(4-propynylphenyl)-8-oxabicyclo(3.2.1)octane (16l) and (1R,1S)-2β-Carbomethoxy-3α-(4-propynylphenyl)-8-oxabicyclo(3.2.1)octane (17l)

Compounds 16l and 17l were prepared from 15l as described for compounds 16a and 17a. Compound 16l was obtained (52%) as a white solid: m.p. 142–143 C; $R_f$ 0.27 (30% EtOAc/hexanes); and compound 17l (13%) as a white solid: m.p. 96.5–97.5 C; $R_f$ 0.40 (30% EtOAc/hexanes). (16l): $^1$HNMR (CDCl$_3$, 300 MHz): δ7.30 (d, 2H), 7.15 (d, 2H), 4.70–4.62 (m, 2H), 3.48 (s, 3H), 3.24–3.13 (m, 1H), 2.84–2.70 (m, 2H), 2.20–1.74 (m, 4H), 2.03 (s, 3H), 1.64–1.57 (m, 1H). Anal. (C 18H$_{20}$O$_3$) C, H. (17l): $^1$HNMR (CDCl$_3$, 300 MHz): δ7.30 (d, 2H), 7.13 (d, 2H), 4.54–4.42 (m, 2H), 3.56 (s, 3H), 3.32–3.16 (m, 1H), 2.50 (d, 1H), 2.45–2.32 (m, 1H), 2.18–1.9 (m, 2H), 2.03 (s, 3H), 1.80–1.58 (m, 2H), 1.45–1.31 (m, 1H). Anal. ($C_{18}H_{20}O_3$) C, H.

(1R,1S)-2β-Carbomethoxy-3β-(4-isopropylphenyl)-8-oxabicyclo(3.2.1)octane (16j) and (1R,1S)-2β-Carbomethoxy-3α-(4-isopropylphenyl)-8-oxabicyclo(3.2.1)octane (17j)

Compounds 16j and 17j were prepared from 15j as described for compounds 16a and 17a. Compound 16j was obtained (45%) as a light yellow oil: $R_f$ 0.25 (30% EtOAc/hexanes); and compound 17j (8.5%) as a light yellow oil: $R_f$ 0.40 (30% EtOAc/hexanes). (16j): $^1$HNMR (CDCl$_3$, 300 MHz): δ7.18–7.15 (m, 4H), 4.70–4.62 (m, 2H), 3.49 (s, 3H), 3.23–3.14 (m, 1H), 2.91–2.72 (m, 3H), 2.20–1.74 (m, 4H), 1.64–1.57 (m, 1H), 1.22 (d, 6H). Anal. ($C_{18}H_{24}O_3$) C, H. (17j): $^1$HNMR (CDCl$_3$, 300 MHz): δ7.13 (s, 4H), 4.54–4.46 (m, 2H), 3.58 (s, 3H), 3.29–3.19 (m, 1H), 2.91–2.80 (m, 1H), 2.55–2.51 (m, 1H), 2.47–2.35 (m, 1H), 2.19–1.61 (m, 4H), 1.46–1.3 (m, 1H), 1.23 (d, 6H). Anal. ($C_{18}H_{24}O_3$) C, H.

(1R,1S)-2β-Carbomethoxy-3β-(4-isopropenylphenyl)-8-oxabicyclo(3.2.1)octane (16k) and (1R,1S)-2β-Carbomethoxy-3α-(4-isopropenylphenyl)-8-oxabicyclo(3.2.1)octane (17k)

Compounds 16k and 17k were prepared from 15k as described for compounds 16a and 17a. Compound 16k was obtained (54%) as a light yellow solid: m.p. 72.3–73.3 C; $R_f$ 0.31 (30% EtOAc/hexanes); and compound 17k (24%) as a off-white solid: m.p. 87–88 C; $R_f$ 0.40 (30% EtOAc/hexanes). (16k): $^1$HNMR (CDCl$_3$, 300 MHz): δ7.40 (d, 2H), 7.21 (d, 2H), 5.35 (s, 1H), 5.04 (s, 1H), 4.70–4.62 (m, 2H), 3.51 (s, 3H), 3.26–3.17 (m, 1H), 2.89–2.73 (m, 2H), 2.22–1.77 (m, 4H), 2.13 (s. 3H), 1.69–1.60 (m, 1H). Anal. ($C_{18}H_{22}O_3$) C, H. (17k): $^1$HNMR (CDCl$_3$, 300 MHz): δ7.40 (δ, 2H), 7.19 (s, 2H), 5.35 (s, 1H), 5.05 (s, 1H), 4.56–4.47 (m, 2H),3.60 (s, 3H), 3.33–3.22 (m, 1H), 2.54 (dd, 1H), 2.46–2.37 (m, 1H), 2.22–1.94 (m, 2H), 2.13 (s,3H), 1.83–1.58 (m, 2H), 1.47–1.38 (m, 1H). Anal. ($C_{18}H_{22}O_3$) C, H.

(1R)-2-Carbomethoxy-8-oxabicyclo(3.2.1)octa-2-ene-3-(1'S)-camphanate ((1R,1'S)-19)

(1R,1S)-2-Carbomethoxy-8-oxabicyclo(3.2.1)octan-3-one, 13 (7.4 g, 40.1 mmol) was dissolved in anhydrous THF (200 mL) and cooled to −78° C. To this solution was added butyl lithium (17.6 mL of a 2.5 M solution, 44.1 mmol); the color changed to yellow orange. After 15 min. at −78° C. (S)-(−)-camphanic chloride (9.6 g, 44.1 mmol) was added in one portion and then the cooling bath was removed. After 5 min. saturated Na$_2$CO$_3$ was added (300 mL) and ether (300 mL). The layers were separated and the ether phase washed with brine (100 mL) and dried (MgSO$_4$). Filtration followed by evaporation gave the crude reaction product (14 g). Purification by column chromatography (SiO$_2$, 400 g, eluent: 30% ethyl acetate in hexanes) gave the diastereomeric mixture, 18 (8.29 g, 57%). $^1$H-NMR of the diagnostic camphanate methyls were δ(1S,1'S) 1.04 (s, 3H), 1.11 (s, 3H), 1.14 (s, 3H); (1R,1'S) 1.06 (s, 3H) 1.14 (s, 6H). This mixture, 18, was recrystallized eight times from methylene chloride/hexanes and gave white crystals of the pure title compound (1R,1'S)-19 (2.25 g, 54%): mp 168.9–169° C.; $R_f$ 0.25 (30% EtOAc/hexanes); $^1$H-NMR (CDCl$_3$, 100 MHz) δ5.04 (br. s, 1H), 5.55–5.75 (m, 1H), 3.71 (s, 3H), 2.90 (dd, J=5, 18 Hz), 1.6–2.7 (m, 9H), 1.14 (s, 6H), 1.06 (s, 3H). Anal. ($C_{19}H_{24}O_7$) C, H.

(1S)-2-Carbomethoxy-8-oxabicyclo(3.2.1)octa-2-ene-3-(1'R)-camphanate ((1S,1'R)-19)

The title compound was obtained as follows: Hydrolysis (LiOH) of the residual mother liquor obtained from recrystallization of (1R,1'S)-19 above gave an enriched mixture (1S: 60% ee) of (1R,1S)-2-carbomethoxy-8-oxabicyclo (3.2.1)octan-3-one, 13. Reaction with (R)-(+)-camphanic chloride then gave the camphanate (2.79 g, 72%). Recrystallization twice from methylene chloride/hexanes gave 1.29 g (92%) of the pure (1S,1'R)-19 diastereomer. This had the same physical and chemical properties as the above ester (1R,1'S)-19. Anal. ($C_{19}H_{24}O_7$) C, H.

(1R)-2-Carbomethoxy-8-oxabicyclo(3.2.1)octan-3-one ((1R)-13)

(1R)-2-Carbomethoxy-8-oxabicyclo(3.2.1)octa-2-ene-3-(S)-camphanate, (1R, 1'S)-19 (1.76 g, 4.8 mmol) was dissolved in THF (15 mL) and then methanol (5 mL) and water (5 mL) were added. The resulting solution was cooled in an ice bath and lithium hydroxide (325 mg, 7.7 mmol) was added in one portion. After 20 min no (1R, 1'S)-19 remained. The solution was neutralized with 1 M hydrochloric acid. Ether (200 mL) was then added and the ethereal solution was washed with brine and dried (MgSO$_4$). Evaporation gave 1.38 g of the crude reaction product. This was chromatographed (SiO$_2$, 50 g, eluent: 20% ether in hexanes) to yield 833 mg (94%) of the pure title compound. $^1$H-NMR and TLC were identical with the racemic ketone 13. Under chiral HPLC conditions (Chiralcel OC column, eluent: 10% isopropanol in hexanes 1 mL/min.) $t_R$ (1S)-13=6.99 min (1.78%); $t_R$ (1R)-13=10.92 min (98.21%, ee=96.4%).

(1S)-2-Carbomethoxy-8-oxabicyclo(3.2.1)octan-3-one ((1S)-13).

The title compound was obtained upon LiOH hydrolysis, as described above, from (1S)-2-Carbomethoxy-8- oxabicyclo(3.2.1)octa-2-ene-3-(1'R)-camphanate: 0.78 g, 86%. $^1$H-NMR and TLC were identical with the racemic ketone 13. Under chiral HPLC conditions (Chiralcel OC column, eluent: 10% isopropanol in hexanes, 1 mL/min) $t_R$ (1S)-13=6.87 (100%, ee>98%); $t_R$ (1R)-13=not present.
Pharmocological And Biological Data

Example 1
Stable Expression of SERT in HEK-293 Cells

The human serotonin transporter vector construct was tranfected as a lipid suspension with Lipofectamine (Life Technologies, Inc., Gaithersburg, Md.) into human embryonic kidney cells (HEK-293, American Type Culture Collection, Rockville, Md.). Cells were plated 24 hours before transfection in Dulbecco's Modified Eagle growth medium supplemented with 10% fetal bovine serum, 100 U/ml penicillin and 100 µg/ml streptomycin, 1% nonessential amino acids (Gibco-BRL, Grand Island, N.Y.) in 100 mm Falcon tissue culture dishes (VWR, S. Plainfield, N.J.). The human serotonin transporter cDNA (courtesy of Dr. R. D. Blakely, Vanderbilt University, Tenn.) was subcloned into (−)pcDNA3.1 (Invitrogen, San Diego, Calif.), which contained an antibiotic resistance gene. The cDNA expression vector construct encoding SERT (10 µg) was diluted in 1 ml of serum free medium (Opti-Mem I, Life Technologies, Inc. Rockville, Md.). The lipofectamine reagent (30 µl) was diluted in 1 ml of serum free medium separately from the DNA to avoid precipitation. The combined solution was added to 8 ml of serum free medium and incubated for 30 min to allow formation of DNA-liposome complexes. At about 50% confluence, the cells were incubated for 5 hours with the transfection mixture and the medium was changed. Cells were incubated at 37° C. in a humidified 5% $CO_2$ incubator for 72 hours and then selected for more than two weeks with 600 µg/ml Geneticin (G418, Life Technologies, Inc., Rockville, Md.). The resistant cells were divided and individual foci were harvested using cloning rings (Bel-Art Products, Pequannock, N.J.) and trypsin (Life Technologies, Inc., Rockville, Md.). Multiple cell lines were tested for ($^3$H)serotonin transport. The clone that displayed the highest serotonin transport was chosen for this study and is referred to as SERT. Thereafter, the selecting antibiotic geneticin sulfate (250 µg/ml) was used continuously for culture of cells expressing the serotonin transporter.

($^3$H)Serotonin Transport: Cell Preparation

Low passage number cells (<25 passage cycle) at 80–90% confluency in 145 mm dishes (Greiner Meditech, Bel Air, Md.) were used to measure ($^3$H)serotonin transport. The medium was removed by aspiration, and cells were washed with Tris-Hepes buffer, pH 7.4 at 25° C. (Tris base: 5 mM; Hepes: 8.5 mM; NaCl: 120 mM; KCl: 5.4 mM; $CaCl_2$:1.2 mM; $MgSO_4$: 1.2 mM; and glucose: 10 mM), supplemented with pargyline (100 µM). The cells were harvested, centrifuged at 1000 g for 5 min, washed twice with the Tris-Hepes buffer and diluted to 250,000 and 1,250,000 cells/ml for stable and transient cell lines, respectively.

Example 2
($^3$H)Serotonin Transport: Pharmacology

The whole-cell suspension (0.2 ml; 5–16 µg of protein) was pre-incubated with various dilutions of each drug (0.2 ml; $10^{-12}$ to $10^{-5}$M) for 15 min. Compounds to be tested were dissolved in ethanol (50 µl), hydrochloric acid (10 µl; 2N) and water to achieve a concentration of 1 mM. Subsequent dilutions were made directly in assay buffer. Non-amines were dissolved in 30% to 50% ethanol and buffer to achieve a concentration of 1 mM. The first dilution used ($10^{-5}$ M) contained less than 1.75% ethanol. ($^3$H)Serotonin transport was initiated by the addition of($^3$H)serotonin (0.2 ml) diluted with unlabeled serotonin to yield a final serotonin concentration of 20 nM. Transport proceeded for 10 min at 25° C. and was terminated as previously described or by centrifugation of the cells. Nonspecific transport was defined as transport in the presence of 10 µM fluoxetine, and these data were subtracted from total counts to yield specific accumulation of ($^3$H)serotonin. Each concentration of drug was assayed in triplicate and each value is the mean ±S.E. of 2–5 independent experiments. Protein concentrations were determined by Bradford assay (Bio-Rad, Richmond, Calif.).

Example 3
Non-Amine Affinity and Transporter Selectivity in Primate Striatum Initial screening procedures for non-amines were conducted in primate striatum, a standard source of brain transporters for drug screening and for generating structure-activity relationships for this series (Table 1). ($^3$H) Citalopram binding studies were conducted with monkey brain tissue (4 mg/ml). Various dilution of drugs (0.2 ml; $10^{-12}$ to $10^{-3}$M) were incubated with 1 nM ($^3$H)citalopram (0.2 ml; ≈80 Ci/mmol; DuPont-NEN, Boston, Mass.) for 2 hours, at 4° C. The binding experiments were terminated by rapid filtration and radioactivity measured as described above. Nonspecific binding was defined by 10 µM fluoxetine, and these data were subtracted from total counts to yield specific ($^3$H)citalopram binding. The experiments were performed in triplicate and each value is the mean ±S.E. of 2–5 independent experiments. Analysis of ($^3$H) citalopram competition assays was performed with EBDA and LIGAND computer programs (Elsevier-Biosoft, Cambridge, U.K.).

Table 1 shows affinities of amines (O-401, O-1228, O-1229) and non-amines to compete with a selective high affinity serotonin transporter ligand, ($^3$H)citalopram, and with a selective high affinity dopamine transporter ligand, ($^3$H)CFT, in monkey striatum homogenates. Competition assays were performed with ($^3$H)citalopram (1 nM, SERT) or with ($^3$H)CFT (1 nM, DAT) and 8–12 concentrations of tested non-amines, each conducted in triplicate as described in Materials and Methods. Values were determined by fitting data to the equation for competitive binding with EBDA computer program. Data represent the mean ±S.D. of two or more experiments.

TABLE 1

| Ligand | Serotonin transporter (SERT) $IC_{50}$ (nM) | Dopamine transporter (DAT) $IC_{50}$ (nM) | SERT/DAT Selectivity |
|---|---|---|---|
| O-401 | 2.47 ± 0.14 | 1.09 ± 0.02 | 0.4 |
| O-1229 | 2.19 ± 0.18 | 0.49 ± 0.04 | 0.2 |
| O-1072 | 4.66 ± 1.24 | 3.88 ± 0.93 | 0.8 |
| O-1228 | 5.95 ± 1.37 | 0.57 ± 0.34 | 0.1 |
| (R)O-1809[a] | 10.2 ± 2.1 | 1,010 ± 246 | 99 |
| (RS)O-1739 | 19.8 ± 0.75 | 1,020 ± 42 | 52 |
| O-1391 | 33.9 ± 1.85 | 13.5 ± 0.9 | 0.4 |
| O-1577 | 72.4[b] | 545 ± 76 | 8 |
| O-1669 | 72.5 ± 12.6 | 27.1 ± 0.1 | 0.4 |
| O-1670 | 77.7 ± 13.5 | 21.2 ± 4.1 | 0.3 |
| O-1585 | 152 ± 26.5 | 446 ± 94 | 3 |
| O-1738 | 158 ± 23 | 912 ± 100 | 6 |

[a]O-1809 is the active enantiomer of O-1739
[b]n = 1

Non-amines competed with ($^3$H)citalopram binding sites with affinities (range: 4.66–158 nM, Table 1), comparable to values for conventional amine nitrogen-containing antidepressants. Some compounds, including the 2β,3β dichlorophenyl series, were relatively non-selective for the serotonin over the dopamine transporter (O-1072, O-1391, O-1669, O-1670) whereas others were 52-, 99-fold (O-1809, O-1739) or moderately selective (O-1738, O-1585). Within the dichloro series (FIG. 1), O-1072, the oxa analog of O-401 retained high affinity for the serotonin (4.66±1.24 nM) and dopamine transporters (3.88±0.93 nM) compared with the progenitor amine O-401 (Table 1). Substitution of the 8-oxa with an 8-carba (O-1391) reduced potency for the SERT by 7-fold to 33.9±1.85 nM. Nevertheless, the results indicate that putative aza-driven ionic bonding or oxa-driven hydrogen bonding are not necessary for high affinity binding to the serotonin transporter.

Among the most potent novel compounds tested were the naphthyl monoamines (O-1228, O-1229; 5.95±1.37 and 2.19±0.18 nM, respectively) but the corresponding carba-based non-amines O-1669 and O-1670 displayed lower affinities (72.5±12.6; 77.7±13.5 nM) than the parent monoamines. The 4-isopropenylphenyl non-amines were potent ((R)-O-1809: 10.2±2.1 nM; (RS)-O-1739: 19.8±0.75) and selective for the serotonin over the dopamine transporter. In contrast, the oxa diastereoisomeric propynyl pair O-1577 and O-1585 displayed modest affinity and selectivity for the serotonin over the dopamine transporter, lower than the corresponding dichloroaryl or 4'-isopropenylphenyl analogs. With the exception of the highly lipophilic non-amines O-1669 and O-1670, the affinities of compounds for inhibiting ($^3$H)citalopram labeled sites in monkey striatum and in HEK cells transfected with the human hSERT were similar (Tables 1, 2).

Table 2 shows affinities of novel amines and non-amines at ($^3$H)citalopram binding sites and ($^3$H)serotonin transport in HEK-293 cells stably or transiently transfected with the human SERT. Non-amines are listed in accordance with their rank order of potency. Competition assays were performed with ($^3$H)citalopram (1 nM) or with ($^3$H)serotonin (20 nM) and 8–12 concentrations of tested non-amines, each conducted in triplicate as described above. Values were determined by fitting data to the equation for competitive binding with EBDA computer program. Data represent the mean ±S.E.M. of n independent experiments and are expressed as $K_i$ values ($K_i$=IC$_{50}$/(1+c/$K_d$ or $K_m$)).

TABLE 2

| Ligand | ($^3$H)citalopram binding Ki (nM) | ($^3$H)serotonin transport Ki (nM) |
|---|---|---|
| O-1229 | 1.42 ± 0.78 | 0.14 ± 0.07 |
| O-1228 | 3.26 ± 0.26 | 4.57 ± 0.37 |
| O-1809 | 9.6 ± 1.3 | 16 ± 4 |
| O-1391 | 10.0 ± 4.30 | 11.1 ± 7.44 |
| O-1739 | 17.7 ± 6.3 | 33 ± 2 |
| O-1577 | 32.6 ± 7.88 | 63.0 ± 16.8 |
| O-1585 | 76.1 ± 10.5 | 56.7 ± 10.4 |
| O-1738 | 218 ± 45.1 | 376 ± 74 |
| O-1669 | 289 ± 150 | 28 ± 2 |
| O-1670 | 303 ± 8.7 | 425 ± 332 |

To determine the effects of non-amines and monoamines on ($^3$H)serotonin transport, we initially characterized ($^3$H)serotonin transport in hSERT cells with clinically relevant antidepressants (see above). Compounds that inhibited ($^3$H)serotonin transport produced monophasic inhibition curves with Hill coefficients close to unity (data not shown). Correlation analysis of the potencies of amines for inhibiting ($^3$H)serotonin transport and competing with ($^3$H)citalopram binding sites yielded a low and insignificant Pearson correlation coefficient ($r^2$: 0.63; p: 0.21). This poor correlation was attributable to the 2–17 fold higher affinities of antidepressant drugs and phenyltropane analogs for ($^3$H) citalopram binding sites compared with their potencies for inhibiting ($^3$H)serotonin transport (data not shown).

In hSERT cells, non-amine affinities for ($^3$H)citalopram binding sites and ($^3$H)serotonin transport were measured and compared with conventional amine antidepressants. In these experiments the density of ($^3$H)citalopram binding sites, $B_{max}$ ranged from 1419 to 2800 fmol/mg of protein (data not shown). Non-amines were selected on the basis of several addressable comparisons, including affinity, enantioselectivity, serotonin: dopamine transporter selectivity and amines (aza) vs oxa or carba non-amines (FIG. 1).

Carba or oxa non-amines inhibited ($^3$H)serotonin transport into HEK-293 cells stably expressing the hSERT in a concentration-dependent and saturable manner. The most potent non-amines, O-1391, O-1072, O-1809, blocked serotonin transport in the 10–20 nM range (Table 2).

The present invention has been described in detail, including the preferred embodiments thereof. However, it will be appreciated that those skilled in the art, upon consideration of the present disclosure, may make modifications and/or improvements of this invention and still be within the scope and spirit of this invention as set forth in the following claims.

All references cited are incorporated herein in their entirety by reference.

We claim:

1. A compound having the structural formula:

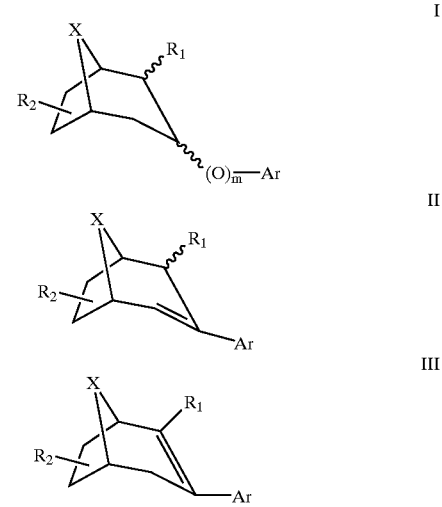

wherein:
R$_1$=COOCH$_3$, COR$_3$, lower alkyl, lower alkenyl, lower alkynyl, CONHR$_4$, or COR$_6$;

R$_2$=is a 6α, 6β, 7α or 7β substituent, which can be selected from H, OH, OR$_3$, F, Cl, Br, and NHR$_3$;

X=CH$_2$, CHY, CYY$_1$, CO, O, S; SO, SO$_2$, or C=CX$_1$Y with the C, O or S atom being a member of the ring;

X$_1$=NR$_3$, CH$_2$, CHY, CYY$_1$ CO, O, S; SO, SO$_2$, or NSO$_2$R$_3$;

R$_3$=H, (CH$_2$)$_n$C$_6$H$_4$Y, C$_6$H$_4$Y, CHCH$_2$, lower alkyl, lower alkenyl or lower alkynyl;

Y and Y$_1$=H, Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, or C(CH$_3$)$_3$;

$R_4$=CH$_3$, CH$_2$CH$_3$, or CH$_3$O$_2$;
$R_6$=morpholinyl or piperidinyl;
Ar=phenyl-R$_5$, naphthyl-R$_5$, anthracenyl-R$_5$, phenanthrenyl-R$_5$, or diphenylmethoxy-R$_5$;
$R_5$=Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, C(CH$_3$)$_3$ where n=0–6, 4-F, 4-Cl, 4-I, 2-F, 2-Cl, 2-I, 3-F, 3-Cl, 3-I, 3,4-diCl, 3,4-diOH, 3,4-diOAc, 3,4-diOCH$_3$, 3-OH-4-Cl, 3-OH-4-F, 3-Cl-4-OH, 3-F-4-OH, lower alkyl, lower alkoxy, lower alkenyl, lower alkynyl, CO(lower alkyl), or CO(lower alkoxy);
m=0 or 1; and
n=0, 1, 2, 3, 4 or 5;
wherein the compound has a SERT/DAT selectivity ratio of at least 3.

2. The compound according to claim 1, wherein the SERT/DAT selectivity ratio is at least about 8.

3. The compound according to claim 1, wherein the SERT/DAT selectivity ratio is at least about 50.

4. The compound according to claim 1, wherein the C in the 3 position is in the α conformation.

5. A compound having the structural formula:

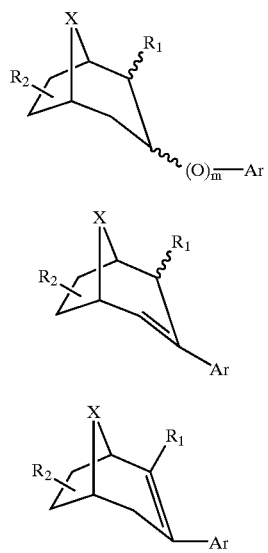

wherein:
$R_1$=COOCH$_3$, COR$_3$, lower alkyl, lower alkenyl, lower alkynyl, CONHR$_4$, or COR$_6$;
$R_2$=is a 6α, 6β, 7α or 7β substituent, which can be selected from H, OH, OR$_3$, F, Cl, Br, and NHR$_3$;
X=CH$_2$, CHY, CYY$_1$, CO, O, S; SO, SO$_2$, or C=CX$_1$Y with the C, O or S atom being a member of the ring;
$X_1$=NR$_3$, CH$_2$, CHY, CYY$_1$ CO, O, S; SO, SO$_2$, or NSO$_2$R$_3$;
$R_3$=H, (CH$_2$)$_n$C$_6$H$_4$Y, C$_6$H$_4$Y, CHCH$_2$, lower alkyl, lower alkenyl or lower alkynyl;
Y and Y$_1$=H, Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, or C(CH$_3$)$_3$;
$R_4$=CH$_3$, CH$_2$CH$_3$, or CH$_3$SO$_2$;
$R_6$=morpholinyl or piperidinyl;
Ar=phenyl-R$_5$, naphthyl-R$_5$, anthracenyl-R$_5$, phenanthrenyl-R$_5$, or diphenylmethoxy-R$_5$;
$R_5$=Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, C(CH$_3$)$_3$ where n=0–6, 4-F, 4-Cl, 4-I, 2-F, 2-Cl, 2-I, 3-F, 3-Cl, 3-I, 3,4-diCl, 3,4-diOH, 3,4-diOAc, 3,4-diOCH$_3$, 3-OH-4-Cl, 3-OH-4-F, 3-Cl-4-OH, 3-F-4-OH, lower alkyl, lower alkoxy, lower alkenyl, lower alkynyl, CO(lower alkyl), or CO(lower alkoxy);
m=0 or 1; and
n=0, 1, 2, 3, 4 or 5;
wherein the compound has an affinity ($K_i$) for the SERT of less than about 500 nM.

6. The compound according to claim 5, wherein the compound has an IC$_{50}$ at the SERT of less than about 50 nM.

7. The compound according to claim 5, wherein the compound has an IC$_{50}$ at the SERT of less than about 25 nM.

8. The compound according to claim 5, wherein the compound has an IC$_{50}$ at the SERT of less than about 15 nM.

9. The compound according to claim 5, wherein the C in the 3 position is in the α conformation.

10. The compound of claim 1, selected from the group consisting of:

a. 2β-carbomethoxy-3β-(4'-propynylphenyl))-8-oxabicyclo(3.2.1)octane;

b. (1R, 1S)-2β-carbomethoxy-3α-(4'-propynylphenyl)-8-oxabicyclo(3.2.1)octane;

c. 2β-carbomethoxy-3α-(4-isopropenylphenyl)-8-oxabicyclo(3.2.1)octane;

d. 2β-carbomethoxy-3β-(4-isopropenylphenyl)-8-oxabicyclo(3.2.1)octane;

e. 2β-carbomethoxy-3β-(4-isopropenylphenyl)-8-oxabicyclo(3.2.1)octane.

11. The compound of claim 5, selected from the group consisting of:

a. 2-β-carbomethoxy-3-β-(3,4-dichlorophenyl)-8-oxabicyclo(3.2.1)octane;

b. 2-β-carbomethoxy-3-β-(3,4-dichlorophenyl)bicyclo(3.2.1)octane;

c. 2β-carbomethoxy-3β-(4'-propynylphenyl))-8-oxabicyclo(3.2.1)octane;

d. 2β-carbomethoxy-3α-(4'-propynylphenyl)-8-oxabicyclo(3.2.1)octane;

e. 2β-carbomethoxy-3β-(2-naphthyl)-8-bicyclo(3.2.1)octane;

f. 2β-carbomethoxy-3α-(2-naphthyl)-8-bicyclo(3.2.1)octane;

g. 2β-carbomethoxy-3α-(4-isopropenylphenyl)-8-oxabicyclo(3.2.1)octane;

h. 2β-carbomethoxy-3β-(4-isopropenylphenyl)-8-oxabicyclo(3.2.1)octane;

i. 2β-carbomethoxy-3β-(4-isopropenylphenyl)-8-oxabicyclo(3.2.1)octane.

12. The compound according to claim 1, wherein the compound has the structure:

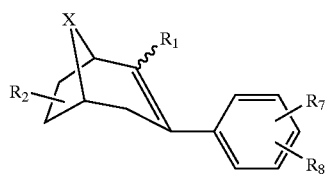

V

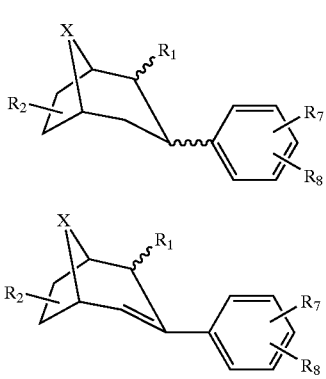

VI

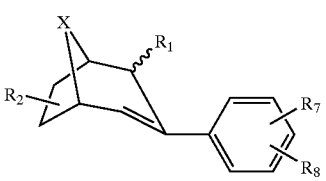

wherein:
X=O, CH$_2$, CHY, CYY$_1$, CO, or C=CX$_1$Y;
R$_7$=lower alkenyl or lower alkynyl group having from about 2 to about 8 carbon atoms: and,
R$_8$=H or Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, C(CH$_3$)$_3$ where n=0–6.

13. The compound according to claim 12, wherein R$_7$ is selected from ethenyl, propenyl, butenyl, propynyl, butynyl and methylpropynyl.

14. The compound according to claim 5, wherein the compound has the structure:

IV

V

VI

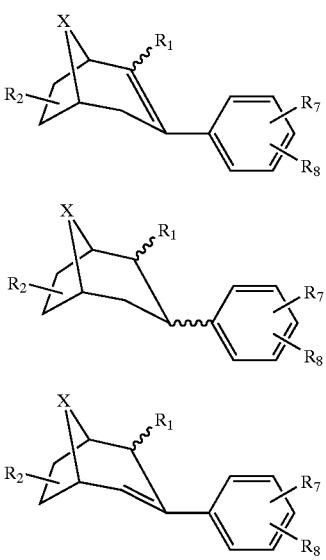

wherein:
X=O, CH$_2$, CHY, CYY$_1$, CO, or C=CX$_1$Y;
R$_7$=lower alkenyl or lower alkynyl group having from about 2 to about 8 carbon atoms: and,
R$_8$=H or Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, C(CH$_3$)$_3$ where n=0–6.

15. The compound according to claim 14, wherein R$_7$ is selected from ethenyl, propenyl, butenyl, propynyl, butynyl and methylpropynyl.

16. A pharmaceutical composition comprising a therapeutically effective amount of a pharmaceutically acceptable carrier and an effective amount of a compound having the structural formula:

I

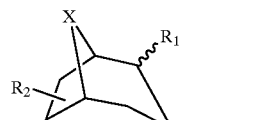

II

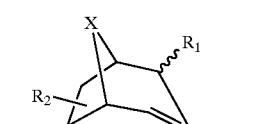

III

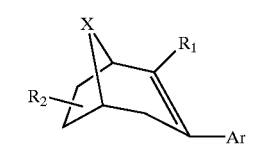

wherein:
R$_1$=COOCH$_3$, COR$_3$, lower alkyl, lower alkenyl, lower alkynyl, CONHR$_4$, or COR$_6$;
R$_2$=is a 6α, 6β, 7α or 7β substituent, which can be selected from H, OH, OR$_3$, F, Cl, Br, and NHR$_3$;
X=CH$_2$, CHY, CYY$_1$, CO, O, S; SO, SO$_2$, or C=CX$_1$Y with the C, O or S atom being a member of the ring;
X$_1$=NR$_3$, CH$_2$, CHY, CYY$_1$ CO, O, S; SO, SO$_2$, or NSO$_2$R$_3$;
R$_3$=H, (CH$_2$)$_n$C$_6$H$_4$Y, C$_6$H$_4$Y, CHCH$_2$, lower alkyl, lower alkenyl or lower alkynyl;
Y and Y$_1$=H, Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, or C(CH$_3$)$_3$;
R$_4$=CH$_3$, CH$_2$CH$_3$, or CH$_3$SO$_2$;
R$_6$=morpholinyl or piperidinyl;
Ar=phenyl-R$_5$, naphthyl-R$_5$, anthracenyl-R$_5$, phenanthrenyl-R$_5$, or diphenylmethoxy-R$_5$;
R$_5$=Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, C(CH$_3$)$_3$ where n=0–6, 4-F, 4-Cl, 4-I, 2-F, 2-Cl, 2-I, 3-F, 3-Cl, 3-I, 3,4-diCl, 3,4-diOH, 3,4-diOAc, 3,4-diOCH$_3$, 3-OH-4-Cl, 3-OH-4-F, 3-Cl-4-OH, 3-F-4-OH, lower alkyl, lower alkoxy, lower alkenyl, lower alkynyl, CO(lower alkyl), or CO(lower alkoxy);
m=0 or 1; and
n=0, 1, 2, 3, 4 or 5;
wherein the compound has a SERT/DAT selectivity ratio of at least 3.

17. A pharmaceutical composition comprising a therapeutically effective amount of a pharmaceutically acceptable carrier and an effective amount of a compound having the structural formula:

I

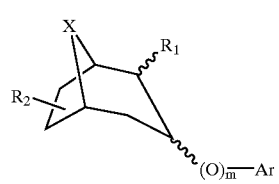

-continued

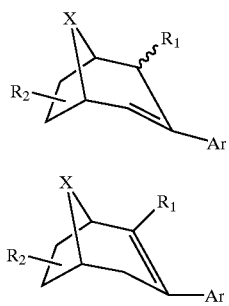
II

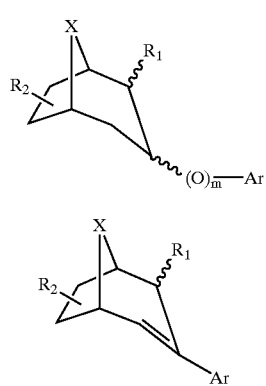
III wherein:
R₁=COOCH₃, COR₃, lower alkyl, lower alkenyl, lower alkynyl, CONHR₄, or COR₆;
R₂=is a 6α, 6β, 7α or 7β substituent, which can be selected from H, OH, OR₃, F, Cl, Br, and NHR₃;
X=CH₂, CHY, CYY₁, CO, O, S; SO, SO₂, or C=CX₁Y with the C, O or S atom being a member of the ring;
X₁=NR₃, CH₂, CHY, CYY₁ CO, O, S; SO, SO₂, or NSO₂R₃;
R₃=H, (CH₂)ₙC₆H₄Y, C₆H₄Y, CHCH₂, lower alkyl, lower alkenyl or lower alkynyl;
Y and Y₁=H, Br, Cl, I, F, OH, OCH₃, CF₃, NO₂, NH₂, CN, NHCOCH₃, N(CH₃)₂, (CH₂)ₙCH₃, COCH₃, or C(CH₃)₃;
R₄=CH₃, CH₂CH₃, or CH₃SO₂;
R₆=morpholinyl or piperidinyl;
Ar=phenyl-R₅, naphthyl-R₅, anthracenyl-R₅, phenanthrenyl-R₅, or diphenylmethoxy-R₅;
R₅=Br, Cl, I, F, OH, OCH₃, CF₃, NO₂, NH₂, CN, NHCOCH₃, N(CH₃)₂, (CH₂)ₙCH₃, COCH₃, C(CH₃)₃ where n=0–6, 4-F, 4-Cl, 4-I, 2-F, 2-Cl, 2-I, 3-F, 3-Cl, 3-I, 3,4-diCl, 3,4-diOH, 3,4-diOAc, 3,4-diOCH₃, 3-OH-4-Cl, 3-OH-4-F, 3-Cl-4-OH, 3-F-4-OH, lower alkyl, lower alkoxy, lower alkenyl, lower alkynyl, CO(lower alkyl), or CO(lower alkoxy);
m=0 or 1; and
n=0, 1, 2, 3, 4 or 5;
wherein the compound has an affinity (K$_i$) for the SERT of less than about 500 nM.

18. A method for inhibiting serotonin reuptake of a monoamine transporter in a mammal comprising administering to the mammal a serotonin reuptake inhibiting amount of a compound having the structural formula:

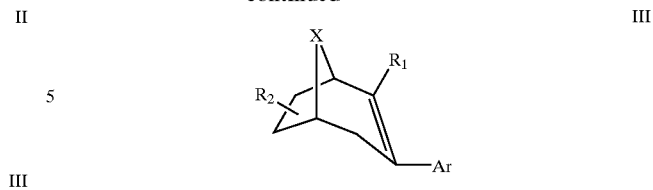

wherein:
R₁=COOCH₃, COR₃, lower alkyl, lower alkenyl, lower alkynyl, CONHR₄, or COR₆;
R₂=is a 6α, 6β, 7α or 7β substituent, which can be selected from H, OH, OR₃, F, Cl, Br, and NHR₃;
X=CH₂, CHY, CYY₁, CO, O, S; SO, SO₂, or C=CX₁Y with the C, O or S atom being a member of the ring;
X₁=NR₃, CH₂, CHY, CYY₁ CO, O, S; SO, SO₂, or NSO₂R₃;
R₃=H, (CH₂)ₙC₆H₄Y, C₆H₄Y, CHCH₂, lower alkyl, lower alkenyl or lower alkynyl;
Y and Y₁=H, Br, Cl, I, F, OH, OCH₃, CF₃, NO₂, NH₂, CN, NHCOCH₃, N(CH₃)₂, (CH₂)ₙCH₃, COCH₃, or C(CH₃)₃;
R₄=CH₃, CH₂CH₃, or CH₃SO₂;
R₆=morpholinyl or piperidinyl;
Ar=phenyl-R₅, naphthyl-R₅, anthracenyl-R₅, phenanthrenyl-R₅, or diphenylmethoxy-R₅;
R₅=Br, Cl, I, F, OH, OCH₃, CF₃, NO₂, NH₂, CN, NHCOCH₃, N(CH₃)₂, (CH₂)ₙCH₃, COCH₃, C(CH₃)₃ where n=0–6, 4-F, 4-Cl, 4-I, 2-F, 2-Cl, 2-I, 3-F, 3Cl, 3-I, 3,4-diCl, 3,4-diOH, 3,4-diOAc, 3,4-diOCH₃, 3-OH-4-Cl, 3-OH-4-F, 3-Cl-4-OH, 3-F-4-OH, lower alkyl, lower alkoxy, lower alkenyl, lower alkynyl, CO(lower alkyl), or CO(lower alkoxy);
m=0 or 1; and
n=0, 1, 2, 3, 4 or 5;
wherein the compound has a SERT/DAT selectivity ratio of at least 3.

19. A method for inhibiting serotonin reuptake of a monoamine transporter in a mammal comprising administering to the mammal a serotonin reuptake inhibiting amount of a compound having the structural formula:

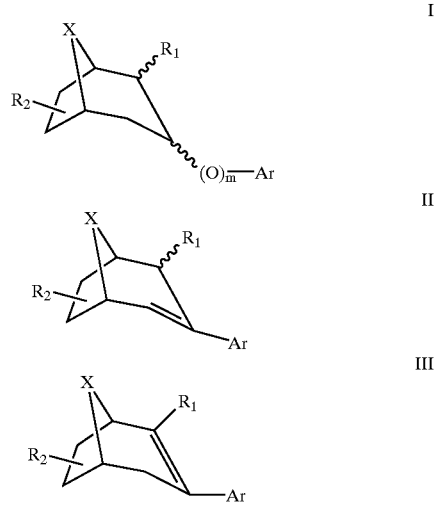

wherein:
R₁=COOCH₃, COR₃, lower alkyl, lower alkenyl, lower alkynyl, CONHR₄, or COR₆;

R$_2$=is a 6α, 6β, 7α or 7β substituent, which can be selected from H, OH, OR$_3$, F, Cl, Br, and NHR$_3$;

X=CH$_2$, CHY, CYY$_1$, CO, O, S; SO, SO$_2$, or C=CX$_1$Y with the C, O or S atom being a member of the ring;

X$_1$=NR$_3$, CH$_2$, CHY, CYY$_1$ CO, O, S; SO, SO$_2$, or NSO$_2$R$_3$;

R$_3$=H, (CH$_2$)$_n$C$_6$H$_4$Y, C$_6$H$_4$Y, CHCH$_2$, lower alkyl, lower alkenyl or lower alkynyl;

Y and Y$_1$=H, Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, or C(CH$_3$)$_3$;

R$_4$=CH$_3$, CH$_2$CH$_3$, or CH$_3$SO$_2$;

R$_6$=morpholinyl or piperidinyl;

Ar=phenyl-R$_5$, naphthyl-R$_5$, anthracenyl-R$_5$, phenanthrenyl-R$_5$, or diphenylmethoxy-R$_5$;

R$_5$=Br, Cl, I, F, OH, OCH$_3$, CF$_3$, NO$_2$, NH$_2$, CN, NHCOCH$_3$, N(CH$_3$)$_2$, (CH$_2$)$_N$CH$_3$, COCH$_3$, C(CH$_3$)$_3$ where n=0–6, 4-F, 4-Cl, 4-I, 2-F, 2-Cl, 2-I, 3-F, 3-Cl, 3-I, 3,4-diCl, 3,4-diOH, 3,4-diOAc, 3,4-diOCH$_3$, 3-OH-4-Cl, 3-OH-4-F, 3-Cl-4-OH, 3-F-4-OH, lower alkyl, lower alkoxy, lower alkenyl, lower alkynyl, CO(lower alkyl), or CO(lower alkoxy);

m=0 or 1; and n=0, 1, 2, 3, 4 or 5;

wherein the compound has an affinity (K$_i$) for the SERT of less than about 500 nM.

20. A method of treating a mammal suffering from a serotonin related disorder comprising administering to the mammal an effective amount of a compound having the structural formula:

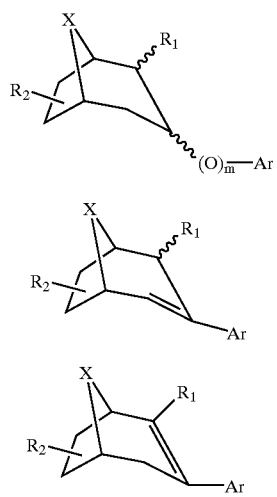

wherein:

R$_1$=COOCH$_3$, COR$_3$, lower alkyl, lower alkenyl, lower alkynyl, CONHR$_4$, or COR$_6$;

R$_2$=is a 6α, 6β, 7α or 7β substituent, which can be selected from H, OH, OR$_3$, F, Cl, Br, and NHR$_3$;

X=CH$_2$, CHY, CYY$_1$, CO, O, S; SO, SO$_2$, or C=CX$_1$Y with the C, O or S atom being a member of the ring;

X$_1$=NR$_3$, CH$_2$, CHY, CYY$_1$ CO, O, S; SO, SO$_2$, or NSO$_2$R$_3$;

R$_3$=H, (CH$_2$)$_n$C$_6$H$_4$Y, C$_6$H$_4$Y, CHCH$_2$, lower alkyl, lower alkenyl or lower alkynyl;

Y and Y$_1$=H, Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, or C(CH$_3$)$_3$;

R$_4$=CH$_3$, CH$_2$CH$_3$, or CH$_3$SO$_2$;

R$_6$=morpholinyl or piperidinyl;

Ar=phenyl-R$_5$, naphthyl-R$_5$, anthracenyl-R$_5$, phenanthrenyl-R$_5$, or diphenylmethoxy-R$_5$;

R$_5$=Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, C(CH$_3$)$_3$ where n=0–6, 4-F, 4-Cl, 4-I, 2-F, 2-Cl, 2-I, 3-F, 3-Cl, 3-I, 3,4-diCl, 3,4-diOH, 3,4-diOAc, 3,4-diOCH$_3$, 3-OH-4-Cl, 3-OH-4-F, 3-Cl-4-OH, 3-F-4-OH, lower alkyl, lower alkoxy, lower alkenyl, lower alkynyl, CO(lower alkyl), or CO(lower alkoxy);

m=0 or 1; and n=0, 1, 2, 3, 4 or 5;

wherein the compound has a SERT/DAT selectivity ratio of at least 3.

21. The method for treating according to claim 20, wherein the disorder is selected from depression, anxiety, eating disorders, and obsessive compulsive disorders.

22. A method of treating a mammal suffering from a serotonin related disorder comprising administering to the mammal an effective amount of a compound having the structural formula:

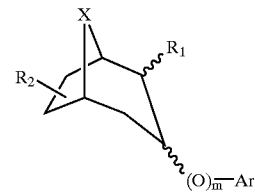

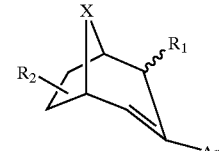

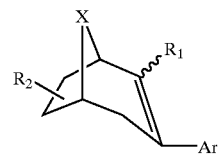

wherein:

R$_1$=COOCH$_3$, COR$_3$, lower alkyl, lower alkenyl, lower alkynyl, CONHR$_4$, or COR$_6$;

R$_2$=is a 6α, 6β, 7α or 7β substituent, which can be selected from H, OH, OR$_3$, F, Cl, Br, and NHR$_3$;

X=CH$_2$, CHY, CYY$_1$, CO, O, S; SO, SO$_2$, or C=CX$_1$Y with the C, O or S atom being a member of the ring;

X$_1$=NR$_3$, CH$_2$, CHY, CYY$_1$ CO, O, S; SO, SO$_2$, or NSO$_2$R$_3$;

R$_3$=H, (CH$_2$)$_n$C$_6$H$_4$Y, C$_6$H$_4$Y, CHCH$_2$, lower alkyl, lower alkenyl or lower alkynyl;

Y and Y$_1$=H, Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, or C(CH$_3$)$_3$;

R$_4$=CH$_3$, CH$_2$CH$_3$, or CH$_3$SO$_2$;

R$_6$=morpholinyl or piperidinyl;

Ar=phenyl-R$_5$, naphthyl-R$_5$, anthracenyl-R$_5$, phenanthrenyl-R$_5$, or diphenylmethoxy-R$_5$;

R$_5$=Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, C(CH$_3$)$_3$ where n=0–6, 4-F, 4-Cl, 4-I, 2-F, 2-Cl, 2-I, 3-F, 3-Cl, 3-I, 3,4-diCl, 3,4-diOH, 3,4-diOAc, 3,4-diOCH$_3$, 3-OH-4-Cl, 3-OH-4-F, 3-Cl-4-OH, 3-F-4-OH, lower alkyl, lower alkoxy, lower alkenyl, lower alkynyl, CO(lower alkyl), or CO(lower alkoxy);

m=0 or 1; and n=0, 1, 2, 3, 4 or 5;

wherein the compound has an affinity ($K_i$) for the SERT of less than about 500 nM.

23. The method for treating according to claim 22, wherein the disorder is selected from depression, anxiety, eating disorders, and obsessive compulsive disorders.

24. A method for treating a mammal suffering from depression comprising administering to the mammal an effective amount of a compound having the structural formula:

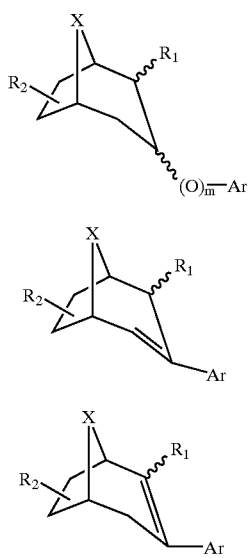

wherein:

R$_1$=COOCH$_3$, COR$_3$, lower alkyl, lower alkenyl, lower alkynyl, CONHR$_4$, or COR$_6$;

R$_2$=is a 6α, 6β, 7α or 7β substituent, which can be selected from H, OH, OR$_3$, F, Cl, Br, and NHR$_3$;

X=CH$_2$, CHY, CYY$_1$, CO, O, S; SO, SO$_2$, or C=CX$_1$Y with the C, O or S atom being a member of the ring;

X$_1$=NR$_3$, CH$_2$, CHY, CYY$_1$ CO, O, S; SO, SO$_2$, or NSO$_2$R$_3$;

R$_3$=H, (CH$_2$)$_n$C$_6$H$_4$Y, C$_6$H$_4$Y, CHCH$_2$, lower alkyl, lower alkenyl or lower alkynyl;

Y and Y$_1$=H, Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, or C(CH$_3$)$_3$;

R$_4$=CH$_3$, CH$_2$CH$_3$, or CH$_3$SO$_2$;

R$_6$=morpholinyl or piperidinyl;

Ar=phenyl-R$_5$, naphthyl-R$_5$, anthracenyl-R$_5$, phenanthrenyl-R$_5$, or diphenylmethoxy-R$_5$;

R$_5$=Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, C(CH$_3$)$_3$ where n=0–6, 4-F, 4-Cl, 4-I, 2-F, 2-Cl, 2-I, 3-F, 3Cl, 3-I, 3,4-diCl, 3,4-diOH, 3,4-diOAc, 3,4-diOCH$_3$, 3-OH-4-Cl, 3-OH-4-F, 3-Cl-4-OH, 3-F-4-OH, lower alkyl, lower alkoxy, lower alkenyl, lower alkynyl, CO(lower alkyl), or CO(lower alkoxy);

m=0 or 1; and n=0, 1, 2, 3, 4 or 5;

wherein the compound has a SERT/DAT selectivity ratio of at least 3.

25. A method for treating a mammal suffering from depression comprising administering to the mammal an effective amount of a compound having the structural formula:

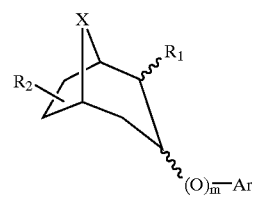

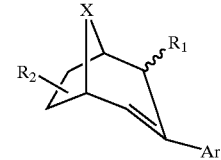

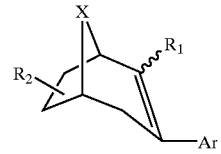

wherein:

R$_1$=COOCH$_3$, COR$_3$, lower alkyl, lower alkenyl, lower alkynyl, CONHR$_4$, or COR$_6$;

R$_2$=is a 6α, 6β, 7α or 7β substituent, which can be selected from H, OH, OR$_3$, F, Cl, Br, and NHR$_3$;

X=CH$_2$, CHY, CYY$_1$, CO, O, S; SO, SO$_2$, or C=CX$_1$Y with the C, O or S atom being a member of the ring;

X$_1$=NR$_3$, CH$_2$, CHY, CYY$_1$ CO, O, S; SO, SO$_2$, or NSO$_2$R$_3$;

R$_3$=H, (CH$_2$)$_n$C$_6$H$_4$Y, C$_6$H$_4$Y, CHCH$_2$, lower alkyl, lower alkenyl or lower alkynyl;

Y and Y$_1$=H, Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, or C(CH$_3$)$_3$;

R$_4$=CH$_3$, CH$_2$CH$_3$, or CH$_3$SO$_2$;

R$_6$=morpholinyl or piperidinyl;

Ar=phenyl-R$_5$, naphthyl-R$_5$, anthracenyl-R$_5$, phenanthrenyl-R$_5$, or diphenylmethoxy-R$_5$;

R$_5$=Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, C(CH$_3$)$_3$ where n=0–6, 4-F, 4-Cl, 4-I, 2-F, 2-Cl, 2-I, 3-F, 3-Cl, 3-I, 3,4-diCl, 3,4-diOH, 3,4-diOAc, 3,4-diOCH$_3$, 3-OH-4-Cl, 3-OH-4-F, 3-Cl-4-OH, 3-F-4-OH, lower alkyl, lower alkoxy, lower alkenyl, lower alkynyl, CO(lower alkyl), or CO(lower alkoxy);

m=0 or 1; and n=0, 1, 2, 3, 4 or 5;

wherein the compound has an affinity ($K_i$) for the SERT of less than about 500 nM.

* * * * *